US010368581B2

(12) United States Patent
Rostami et al.

(10) Patent No.: US 10,368,581 B2
(45) Date of Patent: Aug. 6, 2019

(54) MULTIPLE DISPERSION GENERATOR E-VAPING DEVICE

(71) Applicant: Altria Client Services LLC, Richmond, VA (US)

(72) Inventors: Ali A. Rostami, Richmond, VA (US); Gerd Kobal, Sandy Hook, VA (US); Yezdi Pithawalla, Richmond, VA (US); David Kane, Richmond, VA (US); Christopher S. Tucker, Midlothian, VA (US); Peter Lipowicz, Midlothian, VA (US); Jason Flora, Richmond, VA (US); Georgios Karles, Richmond, VA (US); Munmaya K. Mishra, Manakin Sabot, VA (US); Catherine Barnes, Richmond, VA (US); Richard Arena, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 295 days.

(21) Appl. No.: 15/067,810

(22) Filed: Mar. 11, 2016

(65) Prior Publication Data

US 2017/0258138 A1 Sep. 14, 2017

(51) Int. Cl.

*A24F 47/00* (2006.01)
*H04L 29/06* (2006.01)
*A61B 16/00* (2006.01)

(52) U.S. Cl.

CPC ........ *A24F 47/008* (2013.01); *H04L 65/1069* (2013.01)

(58) Field of Classification Search

None
See application file for complete search history.

(56) References Cited

U.S. PATENT DOCUMENTS

| | | | |
|---|---|---|---|
| 1,771,366 | A | 7/1930 | Wyss |
| 1,968,509 | A | 7/1934 | Tiffany |

(Continued)

FOREIGN PATENT DOCUMENTS

| | | | |
|---|---|---|---|
| BE | 421623 | A | 6/1937 |
| CA | 2947135 | A1 | 11/2015 |

(Continued)

OTHER PUBLICATIONS

International Search Report and Written Opinion for PCT/EP2017/055733 dated Jun. 21, 2017.

(Continued)

*Primary Examiner* — Thor S Campbell
(74) *Attorney, Agent, or Firm* — Harness, Dickey & Pierce, P.L.C.

(57) ABSTRACT

A base for an e-vaping device is configured to couple with multiple cartridges configured to generate separate, respective dispersions. The cartridges may include one or more atomizer assemblies or vaporizer assemblies. The base may include multiple connectors electrically coupled to the power supply. The connectors may be configured to couple multiple dispersion generators to a power supply of the base. The base may include control circuitry configured to independently control dispersion generation by dispersion generators coupled to the base. The control circuitry may independently control dispersion generation by the first and second cartridges based on cartridge information accessed through at least one of the first and second connectors. The control circuitry may control dispersion generation by controlling power supplied to the dispersion generators.

22 Claims, 11 Drawing Sheets

(56) References Cited

U.S. PATENT DOCUMENTS

| | | | |
|---|---|---|---|
| 2,057,353 | A | 10/1936 | Whittmore, Jr. |
| 2,104,266 | A | 1/1938 | McCormick |
| 2,406,275 | A | 8/1946 | Wejnarth |
| 2,442,004 | A | 5/1948 | Hayward-Butt |
| 2,558,127 | A | 6/1951 | Downs |
| 2,642,313 | A | 6/1953 | Montenier |
| 2,728,981 | A | 1/1956 | Hooper |
| 2,830,597 | A | 4/1958 | Kummli |
| 2,907,686 | A | 10/1959 | Siegel |
| 2,971,039 | A | 2/1961 | Western |
| 2,972,557 | A | 2/1961 | Toulman, Jr. |
| 2,974,669 | A | 3/1961 | Ellis |
| 3,062,218 | A | 11/1962 | Temkovits |
| 3,200,819 | A | 8/1965 | Gilbert |
| 3,255,760 | A | 6/1966 | Selke et al. |
| 3,258,015 | A | 6/1966 | Ellis et al. |
| 3,356,094 | A | 12/1967 | Ellis et al. |
| 3,363,633 | A | 1/1968 | Weber |
| 3,402,723 | A | 9/1968 | Hu |
| 3,425,414 | A | 2/1969 | La Roche |
| 3,482,580 | A | 12/1969 | Hollabaugh |
| 3,633,881 | A | 1/1972 | Yurdin |
| 3,812,854 | A | 5/1974 | Michaels et al. |
| 3,878,041 | A | 4/1975 | Leitnaker et al. |
| 3,949,743 | A | 4/1976 | Shanbrom |
| 4,068,672 | A | 1/1978 | Guerra |
| 4,077,784 | A | 3/1978 | Vayrynen |
| 4,083,372 | A | 4/1978 | Boden |
| 4,131,119 | A | 12/1978 | Blasutti |
| 4,141,369 | A | 2/1979 | Burruss |
| 4,164,230 | A | 8/1979 | Pearlman |
| 4,193,411 | A | 3/1980 | Faris et al. |
| 4,219,032 | A | 8/1980 | Tabatznik et al. |
| 4,246,913 | A | 1/1981 | Ogden et al. |
| 4,257,389 | A | 3/1981 | Texidor et al. |
| 4,259,970 | A | 4/1981 | Green, Jr. |
| 4,413,641 | A | 11/1983 | Dwyer, Jr. et al. |
| 4,419,302 | A | 12/1983 | Nishino et al. |
| 4,629,604 | A | 12/1986 | Spector |
| 4,735,217 | A | 4/1988 | Gerth et al. |
| 4,765,347 | A | 8/1988 | Sensabaugh, Jr. et al. |
| 4,804,002 | A | 2/1989 | Herron |
| 4,846,199 | A | 7/1989 | Rose |
| 4,922,901 | A | 5/1990 | Brooks et al. |
| 4,945,929 | A | 8/1990 | Egilmex |
| 4,945,931 | A | 8/1990 | Gori |
| 4,947,874 | A | 8/1990 | Brooks et al. |
| 4,947,875 | A | 8/1990 | Brooks et al. |
| 4,961,727 | A | 10/1990 | Beard |
| 4,981,522 | A | 1/1991 | Nichols et al. |
| 4,991,606 | A | 2/1991 | Serrano et al. |
| 4,993,436 | A | 2/1991 | Bloom, Jr. |
| 5,016,656 | A | 5/1991 | McMurtrie |
| 5,040,552 | A | 8/1991 | Schleich et al. |
| 5,042,510 | A | 8/1991 | Curtiss et al. |
| 5,060,671 | A | 10/1991 | Counts et al. |
| 5,085,804 | A | 2/1992 | Washburn |
| 5,093,894 | A | 3/1992 | Deevi et al. |
| 5,095,921 | A | 3/1992 | Losee et al. |
| 5,139,594 | A | 8/1992 | Rabin |
| 5,144,962 | A | 9/1992 | Counts et al. |
| 5,159,940 | A | 11/1992 | Hayward et al. |
| 5,179,966 | A | 1/1993 | Losee et al. |
| 5,224,498 | A | 7/1993 | Deevi et al. |
| 5,228,460 | A | 7/1993 | Sprinkel et al. |
| 5,235,157 | A | 8/1993 | Blackburn |
| 5,249,586 | A | 10/1993 | Morgan et al. |
| 5,259,062 | A | 11/1993 | Pelonis |
| 5,269,327 | A | 12/1993 | Counts et al. |
| 5,322,075 | A | 6/1994 | Deevi et al. |
| 5,353,813 | A | 10/1994 | Deevi et al. |
| 5,369,723 | A | 11/1994 | Counts et al. |
| 5,388,594 | A | 2/1995 | Counts et al. |
| 5,396,911 | A | 3/1995 | Casey, III et al. |
| 5,404,871 | A * | 4/1995 | Goodman ............. A61M 15/00 128/200.14 |
| 5,408,574 | A | 4/1995 | Deevi et al. |
| 5,498,855 | A | 3/1996 | Deevi et al. |
| 5,505,214 | A | 4/1996 | Collins et al. |
| 5,542,410 | A | 8/1996 | Goodman et al. |
| 5,591,368 | A | 1/1997 | Fleischhauer et al. |
| 5,613,504 | A | 3/1997 | Collins et al. |
| 5,665,262 | A | 9/1997 | Hajaligol et al. |
| 5,666,977 | A | 9/1997 | Higgins et al. |
| 5,666,978 | A | 9/1997 | Counts et al. |
| 5,692,095 | A | 11/1997 | Young |
| 5,743,251 | A | 4/1998 | Howell et al. |
| 5,797,390 | A | 8/1998 | McSoley |
| 5,865,185 | A | 2/1999 | Collins et al. |
| 5,878,752 | A | 3/1999 | Adams et al. |
| 5,894,841 | A | 4/1999 | Voges |
| 5,935,975 | A | 8/1999 | Rose et al. |
| 6,105,877 | A | 8/2000 | Coffee |
| 6,155,268 | A | 12/2000 | Takeuchi |
| 6,196,218 | B1 | 3/2001 | Voges |
| 6,234,167 | B1 | 5/2001 | Cox et al. |
| 6,386,674 | B1 | 5/2002 | Corrigan, III et al. |
| 6,443,146 | B1 | 9/2002 | Voges |
| 6,460,781 | B1 | 10/2002 | Garcia et al. |
| 6,501,052 | B2 | 12/2002 | Cox et al. |
| 6,516,796 | B1 | 2/2003 | Cox et al. |
| 6,532,965 | B1 | 3/2003 | Abhulimen et al. |
| 6,543,443 | B1 | 4/2003 | Klimowicz et al. |
| 6,568,390 | B2 | 5/2003 | Nichols et al. |
| 6,598,607 | B2 | 7/2003 | Adiga et al. |
| 6,663,019 | B2 | 12/2003 | Garcia et al. |
| 6,715,487 | B2 | 4/2004 | Nichols et al. |
| 6,715,697 | B2 | 4/2004 | Duqueroie |
| 6,772,756 | B2 | 8/2004 | Shayan |
| 6,799,576 | B2 | 10/2004 | Farr |
| 6,810,883 | B2 | 11/2004 | Felter et al. |
| 6,830,383 | B2 | 12/2004 | Huang |
| 6,854,470 | B1 | 2/2005 | Pu |
| 7,117,867 | B2 | 10/2006 | Cox et al. |
| 7,131,599 | B2 | 11/2006 | Katase |
| 7,167,641 | B2 | 1/2007 | Tam et al. |
| 7,173,222 | B2 | 2/2007 | Cox et al. |
| 7,195,403 | B2 | 3/2007 | Oki et al. |
| 7,281,670 | B2 | 10/2007 | Lakatos et al. |
| 7,445,484 | B2 | 11/2008 | Wu |
| 7,458,374 | B2 | 12/2008 | Hale et al. |
| D590,988 | S | 4/2009 | Hon |
| D590,989 | S | 4/2009 | Hon |
| D590,990 | S | 4/2009 | Hon |
| D590,991 | S | 4/2009 | Hon |
| 7,513,781 | B2 | 4/2009 | Galauner et al. |
| 7,540,286 | B2 | 6/2009 | Cross et al. |
| 7,614,402 | B2 | 11/2009 | Gomes |
| 7,726,320 | B2 | 6/2010 | Robinson et al. |
| 7,734,159 | B2 | 6/2010 | Beland et al. |
| 7,780,041 | B2 | 8/2010 | Albisetti |
| 7,832,410 | B2 | 11/2010 | Hon |
| 7,845,359 | B2 | 12/2010 | Montaser |
| 7,913,688 | B2 | 3/2011 | Cross et al. |
| 7,920,777 | B2 | 4/2011 | Rabin et al. |
| 7,997,280 | B2 | 8/2011 | Rosenthal |
| 8,079,371 | B2 | 12/2011 | Robinson et al. |
| D655,036 | S | 2/2012 | Zhou |
| 8,127,772 | B2 | 3/2012 | Montaser |
| 8,156,944 | B2 | 4/2012 | Han |
| 8,205,622 | B2 | 6/2012 | Pan |
| 8,258,192 | B2 | 9/2012 | Wu et al. |
| 8,314,591 | B2 * | 11/2012 | Terry .................... A24F 47/008 320/114 |
| 8,320,751 | B2 | 11/2012 | Porchia et al. |
| 8,349,251 | B2 | 1/2013 | Woo et al. |
| 8,365,742 | B2 | 2/2013 | Hon |
| 8,367,959 | B2 | 2/2013 | Spertell |
| 8,371,310 | B2 | 2/2013 | Brenneise |
| 8,375,957 | B2 | 2/2013 | Hon |
| 8,393,331 | B2 | 3/2013 | Hon |
| 8,402,976 | B2 * | 3/2013 | Fernando .............. A24F 47/008 131/194 |

(56) References Cited

U.S. PATENT DOCUMENTS

RE44,312 E 6/2013 Vieira
D684,311 S 6/2013 Liu
8,459,270 B2 6/2013 Coven et al.
8,483,553 B2 7/2013 Tollens et al.
8,498,524 B2 7/2013 Ruiz Ballesteros et al.
8,499,766 B1 8/2013 Newton
8,511,318 B2 8/2013 Hon
8,528,569 B1 9/2013 Newton
8,550,068 B2 10/2013 Terry et al.
8,550,069 B2 10/2013 Alelov
8,584,670 B2 11/2013 Hyde et al.
8,689,804 B2 * 4/2014 Fernando .............. A24F 47/008 131/184.1
8,689,805 B2 4/2014 Hon
8,833,364 B2 * 9/2014 Buchberger ......... A61M 11/041 128/200.14
8,869,804 B2 10/2014 Mishra et al.
8,915,254 B2 12/2014 Monsees et al.
8,944,052 B2 2/2015 Osorio
9,017,091 B2 4/2015 Zhu et al.
9,271,528 B2 3/2016 Liu
9,498,002 B1 11/2016 Soreide
9,603,386 B2 3/2017 Xiang
9,675,114 B2 6/2017 Timmermans
9,675,117 B2 6/2017 Li et al.
9,763,477 B2 9/2017 Zhu
9,808,032 B2 11/2017 Yamada et al.
9,888,714 B2 2/2018 Cameron et al.
9,974,743 B2 5/2018 Rose et al.
10,015,986 B2 7/2018 Cadieux et al.
2002/0071871 A1 6/2002 Snyder et al.
2002/0078948 A1 6/2002 Hindle et al.
2002/0079309 A1 6/2002 Cox et al.
2002/0086852 A1 7/2002 Cantor et al.
2002/0146242 A1 10/2002 Vieira
2002/0170566 A1 11/2002 Farr
2002/0179102 A1 12/2002 Farr
2003/0056790 A1 3/2003 Nichols et al.
2003/0075188 A1 4/2003 Adiga et al.
2003/0150451 A1 8/2003 Shayan
2004/0050396 A1 3/2004 Squeo
2004/0247301 A1 12/2004 Yip et al.
2005/0016550 A1 1/2005 Katase
2005/0150489 A1 7/2005 Dunfield et al.
2005/0235991 A1 10/2005 Nichols et al.
2005/0263618 A1 12/2005 Spallek et al.
2006/0054165 A1 3/2006 Hughes et al.
2006/0191546 A1 8/2006 Takano et al.
2006/0196518 A1 9/2006 Hon
2006/0213503 A1 9/2006 Borgschulte et al.
2007/0068523 A1 3/2007 Fishman
2007/0102013 A1 5/2007 Adams et al.
2007/0237499 A1 10/2007 DeWitt et al.
2007/0267031 A1 11/2007 Hon
2007/0267032 A1 11/2007 Shan
2008/0022999 A1 1/2008 Belcastro et al.
2008/0029084 A1 2/2008 Costantino et al.
2008/0138398 A1 6/2008 Gonda
2008/0138399 A1 6/2008 Gonda
2008/0230052 A1 9/2008 Montaser
2008/0241255 A1 10/2008 Rose et al.
2008/0247892 A1 10/2008 Kawasumi
2008/0276947 A1 11/2008 Martzel
2008/0299048 A1 12/2008 Hale et al.
2009/0056729 A1 3/2009 Zawadzki et al.
2009/0095287 A1 4/2009 Emarlou
2009/0095311 A1 4/2009 Han
2009/0095312 A1 4/2009 Herbrich et al.
2009/0126745 A1 5/2009 Hon
2009/0130216 A1 5/2009 Cartt et al.
2009/0151717 A1 6/2009 Bowen et al.
2009/0162294 A1 6/2009 Werner
2009/0188490 A1 7/2009 Han
2009/0230117 A1 9/2009 Fernando et al.
2009/0255534 A1 10/2009 Paterno
2009/0272379 A1 11/2009 Thorens et al.
2009/0283103 A1 11/2009 Nielsen et al.
2010/0021900 A1 1/2010 Gong et al.
2010/0031968 A1 2/2010 Sheikh et al.
2010/0083959 A1 4/2010 Siller
2010/0126505 A1 5/2010 Rinker
2010/0200006 A1 8/2010 Robinson et al.
2010/0200008 A1 8/2010 Taieb
2010/0206317 A1 8/2010 Albino et al.
2010/0229881 A1 9/2010 Hearn
2010/0242975 A1 9/2010 Hearn
2010/0242976 A1 9/2010 Katayama et al.
2010/0266643 A1 10/2010 Willett et al.
2010/0307518 A1 12/2010 Wang
2011/0005535 A1 1/2011 Xiu
2011/0011396 A1 1/2011 Fang
2011/0036346 A1 2/2011 Cohen et al.
2011/0036363 A1 2/2011 Urtsev et al.
2011/0041858 A1 2/2011 Montaser
2011/0094523 A1 4/2011 Thorens et al.
2011/0120482 A1 5/2011 Brenneise
2011/0155153 A1 6/2011 Thorens et al.
2011/0168172 A1 7/2011 Patton et al.
2011/0209717 A1 9/2011 Han
2011/0226236 A1 9/2011 Buchberger
2011/0232654 A1 9/2011 Mass
2011/0245493 A1 10/2011 Rabinowitz et al.
2011/0265806 A1 11/2011 Alarcon et al.
2011/0277756 A1 11/2011 Terry et al.
2011/0277757 A1 11/2011 Terry et al.
2011/0277760 A1 11/2011 Terry et al.
2011/0277761 A1 11/2011 Terry et al.
2011/0277764 A1 11/2011 Terry et al.
2011/0277780 A1 11/2011 Terry et al.
2011/0290244 A1 12/2011 Schennum
2011/0303231 A1 12/2011 Li et al.
2011/0304282 A1 12/2011 Li et al.
2011/0315152 A1 12/2011 Hearn et al.
2012/0006342 A1 1/2012 Rose et al.
2012/0048266 A1 3/2012 Alelov
2012/0048466 A1 3/2012 Eckert et al.
2012/0111347 A1 5/2012 Hon
2012/0114809 A1 5/2012 Edwards et al.
2012/0118301 A1 5/2012 Montaser
2012/0145169 A1 6/2012 Wu
2012/0167906 A1 7/2012 Gysland
2012/0174914 A1 7/2012 Pirshafiey et al.
2012/0186594 A1 7/2012 Liu
2012/0199146 A1 8/2012 Marangos
2012/0199663 A1 8/2012 Qiu
2012/0207427 A1 8/2012 Ito
2012/0211015 A1 8/2012 Li et al.
2012/0227752 A1 9/2012 Alelov
2012/0230659 A1 9/2012 Goodman et al.
2012/0255567 A1 10/2012 Rose et al.
2012/0260927 A1 10/2012 Liu
2012/0285475 A1 11/2012 Liu
2012/0291791 A1 11/2012 Pradeep
2012/0312313 A1 12/2012 Frija
2012/0318882 A1 12/2012 Abehasera
2013/0014772 A1 1/2013 Liu
2013/0019887 A1 1/2013 Liu
2013/0025609 A1 1/2013 Liu
2013/0037041 A1 2/2013 Worm et al.
2013/0042865 A1 2/2013 Monsees et al.
2013/0056013 A1 3/2013 Terry et al.
2013/0074854 A1 3/2013 Lipowicz
2013/0152956 A1 6/2013 von Borstel et al.
2013/0192615 A1 8/2013 Tucker et al.
2013/0192616 A1 8/2013 Tucker et al.
2013/0192619 A1 8/2013 Tucker et al.
2013/0192620 A1 8/2013 Tucker et al.
2013/0192621 A1 8/2013 Li et al.
2013/0192622 A1 8/2013 Tucker et al.
2013/0192623 A1 8/2013 Tucker et al.
2013/0213418 A1 8/2013 Tucker et al.
2013/0213419 A1 8/2013 Tucker et al.
2013/0220315 A1 8/2013 Conley et al.
2013/0228191 A1 9/2013 Newton

(56) References Cited

U.S. PATENT DOCUMENTS

| | | | |
|---|---|---|---|
| 2013/0284192 A1 | 10/2013 | Peleg et al. | |
| 2013/0298905 A1 | 11/2013 | Levin et al. | |
| 2013/0312778 A1 | 11/2013 | Shibuichi | |
| 2013/0319407 A1 | 12/2013 | Liu | |
| 2013/0319440 A1 | 12/2013 | Capuano | |
| 2013/0340775 A1 | 12/2013 | Juster et al. | |
| 2014/0000638 A1 | 1/2014 | Sebastian et al. | |
| 2014/0014125 A1 | 1/2014 | Fernando et al. | |
| 2014/0060527 A1 | 3/2014 | Liu | |
| 2014/0060556 A1* | 3/2014 | Liu | A24F 47/008 131/329 |
| 2014/0081234 A1 | 3/2014 | Eggert et al. | |
| 2014/0096782 A1 | 4/2014 | Ampolini et al. | |
| 2014/0123989 A1 | 5/2014 | LaMothe | |
| 2014/0153195 A1 | 6/2014 | You et al. | |
| 2014/0163048 A1 | 6/2014 | Barker et al. | |
| 2014/0166029 A1 | 6/2014 | Weigensberg et al. | |
| 2014/0174441 A1 | 6/2014 | Seeney et al. | |
| 2014/0190496 A1 | 7/2014 | Wensley et al. | |
| 2014/0202474 A1 | 7/2014 | Peleg et al. | |
| 2014/0209105 A1 | 7/2014 | Sears et al. | |
| 2014/0224245 A1 | 8/2014 | Alelov | |
| 2014/0246035 A1 | 9/2014 | Minskoff et al. | |
| 2014/0261486 A1 | 9/2014 | Potter et al. | |
| 2014/0261488 A1* | 9/2014 | Tucker | A24F 47/008 131/328 |
| 2014/0261492 A1 | 9/2014 | Kane | |
| 2014/0261788 A1 | 9/2014 | Lewis | |
| 2014/0267488 A1 | 9/2014 | Ready et al. | |
| 2014/0366898 A1 | 12/2014 | Monsees et al. | |
| 2015/0020823 A1 | 1/2015 | Lipowicz et al. | |
| 2015/0027454 A1 | 1/2015 | Li et al. | |
| 2015/0027468 A1 | 1/2015 | Li et al. | |
| 2015/0027469 A1 | 1/2015 | Tucker et al. | |
| 2015/0027470 A1 | 1/2015 | Kane et al. | |
| 2015/0047662 A1 | 2/2015 | Hopps | |
| 2015/0068544 A1 | 3/2015 | Moldoveanu et al. | |
| 2015/0164141 A1 | 6/2015 | Newton | |
| 2015/0196059 A1 | 7/2015 | Liu | |
| 2015/0258289 A1 | 9/2015 | Henry, Jr. et al. | |
| 2015/0313275 A1 | 11/2015 | Anderson et al. | |
| 2015/0320116 A1 | 11/2015 | Bleloch et al. | |
| 2015/0335070 A1 | 11/2015 | Sears et al. | |
| 2015/0351456 A1 | 12/2015 | Johnson et al. | |
| 2016/0021930 A1 | 1/2016 | Minskoff et al. | |
| 2016/0109115 A1 | 4/2016 | Lipowicz | |
| 2016/0120224 A1 | 5/2016 | Mishra et al. | |
| 2016/0135506 A1 | 5/2016 | Sanchez et al. | |
| 2016/0174611 A1 | 6/2016 | Monsees et al. | |
| 2016/0183598 A1 | 6/2016 | Tucker et al. | |
| 2016/0192708 A1 | 7/2016 | Demeritt et al. | |
| 2016/0235123 A1 | 8/2016 | Krietzman | |
| 2016/0331026 A1 | 11/2016 | Cameron | |
| 2016/0334119 A1 | 11/2016 | Cameron | |
| 2017/0027232 A1 | 2/2017 | Scheck et al. | |
| 2017/0042251 A1 | 2/2017 | Yamada et al. | |
| 2017/0086500 A1 | 3/2017 | Li et al. | |
| 2017/0109877 A1 | 4/2017 | Peleg et al. | |
| 2017/0112197 A1 | 4/2017 | Li et al. | |
| 2017/0150755 A1 | 6/2017 | Batista | |
| 2017/0150758 A1 | 6/2017 | Fernando et al. | |
| 2017/0157341 A1 | 6/2017 | Pandya et al. | |
| 2017/0290998 A1 | 10/2017 | Poston et al. | |
| 2017/0354180 A1 | 12/2017 | Fornarelli | |
| 2018/0007966 A1 | 1/2018 | Li et al. | |
| 2018/0235277 A1 | 8/2018 | Lin et al. | |

FOREIGN PATENT DOCUMENTS

| | | | |
|---|---|---|---|
| CH | 421786 | A | 9/1966 |
| CN | 87104459 | A | 2/1988 |
| CN | 2719043 | Y | 8/2005 |
| CN | 2777995 | Y | 5/2006 |
| CN | 101084801 | A | 12/2007 |
| CN | 101116542 | A | 2/2008 |
| CN | 201018927 | Y | 2/2008 |
| CN | 201029436 | Y | 3/2008 |
| CN | 201054977 | Y | 5/2008 |
| CN | 201067079 | Y | 6/2008 |
| CN | 201076006 | Y | 6/2008 |
| CN | 201085044 | Y | 7/2008 |
| CN | 101518361 | A | 9/2009 |
| CN | 201379072 | Y | 1/2010 |
| CN | 201709398 | U | 1/2011 |
| CN | 201789924 | U | 4/2011 |
| CN | 201797997 | U | 4/2011 |
| CN | 102106611 | A | 6/2011 |
| CN | 201860753 | U | 6/2011 |
| CN | 102166044 | A | 8/2011 |
| CN | 202014571 | | 10/2011 |
| CN | 202014572 | U | 10/2011 |
| CN | 202026804 | U | 11/2011 |
| CN | 202233005 | U | 5/2012 |
| CN | 202233007 | U | 5/2012 |
| CN | 102655773 | A | 9/2012 |
| DE | 2653133 | A1 | 5/1978 |
| DE | 3640917 | A1 | 8/1988 |
| DE | 3735704 | A1 | 5/1989 |
| DE | 19854009 | A1 | 5/2000 |
| EP | 0893071 | A1 | 7/1908 |
| EP | 0277519 | A2 | 8/1988 |
| EP | 0295122 | A2 | 12/1988 |
| EP | 0358 002 | A2 | 3/1990 |
| EP | 0358002 | A2 | 3/1990 |
| EP | 0358114 | A2 | 3/1990 |
| EP | 0430566 | A2 | 6/1991 |
| EP | 0845220 | A1 | 6/1998 |
| EP | 0857431 | A1 | 8/1998 |
| EP | 1989946 | A1 | 11/2008 |
| EP | 2022350 | A1 | 2/2009 |
| EP | 2113178 | A1 | 11/2009 |
| EP | 2454956 | A1 | 5/2012 |
| EP | 2460424 | A1 | 6/2012 |
| EP | 2481308 | A1 | 8/2012 |
| EP | 2671461 | A1 | 12/2013 |
| GB | 680815 | A | 10/1952 |
| GB | 2148079 | A | 5/1985 |
| GB | 2513631 | A | 11/2014 |
| GB | 2524779 | A | 10/2015 |
| JP | 61068061 | A | 4/1986 |
| JP | 2006320286 | A | 11/2006 |
| KR | 100636287 | B1 | 10/2006 |
| NL | 8201585 | A | 11/1982 |
| WO | WO-86/02528 | A1 | 5/1986 |
| WO | WO-9003224 | A1 | 4/1990 |
| WO | WO-95/02970 | A1 | 2/1995 |
| WO | WO-1997/042993 | A2 | 11/1997 |
| WO | WO-00/28843 | A1 | 5/2000 |
| WO | WO-03037412 | A2 | 5/2003 |
| WO | WO-2004/080216 | A1 | 9/2004 |
| WO | WO-2004/095955 | A1 | 11/2004 |
| WO | WO-2005/053444 | A1 | 6/2005 |
| WO | WO-2005/099494 | A1 | 10/2005 |
| WO | WO-2007/066374 | A1 | 6/2007 |
| WO | WO-2007/078273 | A1 | 7/2007 |
| WO | WO-2007/098337 | A2 | 8/2007 |
| WO | WO-2007/131449 | A1 | 11/2007 |
| WO | WO-2007/131450 | A1 | 11/2007 |
| WO | WO-2007/141668 | A2 | 12/2007 |
| WO | WO-2008/055423 | A1 | 5/2008 |
| WO | WO-2010/091593 | A1 | 8/2010 |
| WO | WO-2010/145468 | A1 | 12/2010 |
| WO | WO-2011/124033 | A1 | 10/2011 |
| WO | WO-2011/125058 | A1 | 10/2011 |
| WO | WO-2011/146372 | A2 | 11/2011 |
| WO | WO-2012/129787 | A1 | 10/2012 |
| WO | WO-2012/129812 | A1 | 10/2012 |
| WO | WO-2012/142293 | A2 | 10/2012 |
| WO | WO-2012/174677 | A1 | 12/2012 |
| WO | WO-2013/022936 | A1 | 2/2013 |
| WO | WO-2013/027249 | A1 | 2/2013 |
| WO | WO-2013116558 | | 8/2013 |
| WO | WO-2014110119 | A1 | 7/2014 |

(56) References Cited

FOREIGN PATENT DOCUMENTS

| | | | |
|---|---|---|---|
| WO | WO-2014187770 | A2 | 11/2014 |
| WO | WO-2015/040180 | A2 | 3/2015 |
| WO | WO-2015/079197 | A1 | 6/2015 |
| WO | WO-2015150699 | A1 | 10/2015 |
| WO | WO-2016005602 | A1 | 1/2016 |
| WO | WO-2016015246 | A1 | 2/2016 |
| WO | WO-2016183573 | A1 | 11/2016 |

OTHER PUBLICATIONS

Invitation to Pay Additional Fees for PCT/EP2017/055098 dated May 10, 2017.
International Search Report and Written Opinion for PCT/EP2017/055098 dated Jul. 14, 2017.
International Search Report and Written Opinion for PCT/EP2017/055100 dated Jun. 19, 2017.
Office Action for corresponding Russian Application No. 2015144179 dated Jul. 11, 2017 and English translation thereof.
Lee, Y, Jeng, F and Chen, C. "Technique for aerosol generation with controllable micrometer size distribution", Chemosphere 73 (2008) 760-767.
U.S. Appl. No. 14/199,365, filed Mar. 6, 2014.
U.S. Appl. No. 15/059,790, filed Mar. 3, 2016.
U.S. Appl. No. 15/059,746, filed Mar. 3, 2016.
U.S. Appl. No. 15/063,900, filed Mar. 8, 2016.
U.S. Appl. No. 15/059,791, filed Mar. 3, 2016.
U.S. Appl. No. 15/067,990, filed Mar. 11, 2016.
U.S. Appl. No. 15/067,867, filed Mar. 11, 2016.
International Search Report and Written Opinion dated May 24, 2017 issued in corresponding International Application No. PCT/EP2017/055734.
Chinese Office Action dated Apr. 1, 2017 issued in corresponding Chinese Patent Application No. 201480016196.1 (with translation).
International Preliminary Report on Patentability for PCT/US2013/027424 dated Sep. 4, 2014.
International Search Report and Written Opinion dated Jun. 8, 2017 issued in corresponding International Application No. PCT/EP2017/055472.
International Search Report and Written Opinion for PCT/EP2017/055725 dated Jun. 13, 2017.
International Search Report and Written Opinion for PCT/US2013/022330 dated Jul. 15, 2014.
International Search Report and Written Opinion for PCT/US2013/027424 dated Apr. 25, 2013.
International Search Report dated Jul. 15, 2014.
International Search Report and Written Opinion dated May 9, 2017 issued in corresponding PCT Application No. PCT/EP2017/055102.
Lee et al., Technique for aerosol generation with controllable micrometer size distribution, Chemosphere 73 (2008), pp. 760-767.
Moroccan Examination Report Application No. 38386 dated Mar. 18, 2016.
Moroccan Notification of a Preliminary Search Report with Opinion on Patentability on Application No. 38386 dated Dec. 23, 2015.
Jun. 20, 2016 U.S. Office Action issued in related U.S. Appl. No. 14/199,365.
U.S. Office Action issued in co-pending U.S. Appl. No. 15/067,990 dated Mar. 19, 2018.
U.S. Office Action issued in co-pending U.S. Appl. No. 15/059,791 dated Mar. 21, 2018.
U.S. Office Action issued in co-pending U.S. Appl. No. 15/059,790 dated Mar. 21, 2018.
U.S. Office Action issued in co-pending U.S. Appl. No. 15/063,900 dated Apr. 24, 2018.
Communication Pursuant to Rule 114(2) dated Oct. 1, 2018 in European Application No. 17710247.2.
U.S. Office Action issued in co-pending U.S. Appl. No. 15/067,867 dated Aug. 3, 2018.
U.S. Office Action dated Nov. 9, 2018 issued in co-pending U.S. Appl. No. 15/059,791.
U.S. Office Action dated Nov. 16, 2018 issued in co-pending U.S. Appl. No. 15/067,990.
U.S. Office Action dated Dec. 27, 2018 issued in co-pending U.S. Appl. No. 15/059,746.
Notice of Allowance dated Apr. 23, 2019 for corresponding U.S. Appl. No. 15/059,791.
U.S. Office Action dated Apr. 5, 2019 for corresponding U.S. Appl. No. 15/067,990.
U.S. Office Action dated Mar. 21, 2019 issued in co-pending U.S. Appl. No. 15/059,790.
Non-Final Office Action dated Aug. 3, 2018 in U.S. Appl. No. 15/067,867.
Non-Final Office Action dated Sep. 28, 2018 in U.S. Appl. No. 15/059,790.
U.S. Office Action dated Nov. 9, 2018 dated in co-pending U.S. Appl. No. 15/059,791.
U.S. Office Action dated Nov. 16, 2018 dated in co-pending U.S. Appl. No. 15/067,990.
Office Action for corresponding US Appl. No. 14/199,365 dated Jun. 20, 2016.
Kazakhstan Notice of Allowance dated Apr. 11, 2019 for corresponding Kazakhstan Application No. 2018/00693.1.
U.S. Notice of Allowance dated May 2, 2019 for corresponding U.S. Appl. No. 15/067,867.
U.S. Notice of Allowance dated May 3, 2019 for corresponding U.S. Appl. No. 15/059,746.
U.S. Notice of Allowance dated Apr. 23, 2019 for corresponding U.S. Appl. No. 15/059,791.
U.S. Notice of Allowance dated May 16, 2019 for corresponding U.S. Appl. No. 15/063,900.
U.S. Appl. No. 15/059,790, dated Mar. 3, 2016.
U.S. Appl. No. 15/063,900, dated Mar. 8, 2016.
U.S. Appl. No. 15/067,867, dated Mar. 11, 2016.
U.S. Appl. No. 15/059,791, dated Mar. 3, 2016.
U.S. Appl. No. 15/059,746, dated Mar. 3, 2016.
U.S. Appl. No. 15/067,990, dated Mar. 11, 2016.
U.S. Appl. No. 16/227,354, dated Dec. 20, 2018.

* cited by examiner

MULTIPLE DISPERSION GENERATOR E-VAPING DEVICE

BACKGROUND

Field

Example embodiments relate to an electronic vaping or e-vaping device configured to generate one or more dispersions.

Description of Related Art

E-vaping devices, also referred to herein as electronic vaping devices (EVDs) may be used by adult vapers for portable vaping. An e-vaping device may generate a dispersion. A dispersion generator may generate a dispersion from a pre-aerosol formulation or pre-vapor formulation, hereinafter referred to collectively as a "formulation." The e-vaping device may include a reservoir that holds a formulation.

In some cases, in order to provide one or more sensory experiences to adult vapers, an e-vaping device may include multiple formulations. However, in some cases the separate formulations may react with each other when held in a reservoir of an e-vaping device. Such reactions may result in the degradation of one or more of the formulations, or formation of one or more reaction products which may detract from the sensory experience when included in a dispersion, thereby reducing a shelf-life of a portion of the e-vaping device. As a result, a sensory experience of the adult vaper using an e-vaping device holding the formulations may be degraded.

SUMMARY

According to some example embodiments, a base may include a power supply, at least first and second connectors, and control circuitry. The power supply may be configured to supply electrical power. The first and second connectors may be configured to electrically couple separate, respective first and second cartridges to the power supply. The control circuitry may be configured to independently control dispersion generation by the first and second cartridges, based on cartridge information accessed through at least one of the first and second connectors.

In some example embodiments, the control circuitry may be configured to establish a first communication link with a first storage device in the first cartridge via the first connector. The control circuitry may be configured to access cartridge information from the first storage device via the first communication link, the cartridge information being associated with the first cartridge.

In some example embodiments, the cartridge information includes at least one of information uniquely identifying one or more elements of a dispersion generator included in the first cartridge, information indicating a dispersion generator "type" of a dispersion generator included in the first cartridge, information associated with a formulation held in the first cartridge, and a particular activation sequence associated with a dispersion generator included in the first cartridge.

In some example embodiments, the control circuitry may be configured to independently control dispersion generation by the first and second cartridges based on independent control of electrical power supplied from the power supply to the first and second cartridges via the first and second connectors.

In some example embodiments, the control circuitry may be configured to independently control the electrical power supplied to the first and second connectors, such that electrical power is supplied to the first and second cartridges at different times.

In some example embodiments, the control circuitry may be configured to independently control the electrical power supplied to the first and second connectors, such that electrical power is supplied to alternate cartridges of the first and second cartridges in response to successive vaping command signals.

In some example embodiments, the control circuitry may be configured to independently control the electrical power supplied to the first and second connectors, such that a dispersion generator included in the second cartridge generates a dispersion based on heat generated by a dispersion generator included in the first cartridge.

In some example embodiments, the first and second cartridges may include at least one atomizer assembly and at least one vaporizer assembly, the atomizer assembly being configured to generate an aerosol via applying mechanical force to a pre-aerosol formulation, the vaporizer assembly being configured to generate a vapor via heating a pre-vapor formulation.

In some example embodiments, the power supply may include a rechargeable battery.

According to some example embodiments, an e-vaping device includes a power supply configured to supply electrical power, at least first and second cartridges electrically coupled to the power supply, and control circuitry configured to independently control dispersion generation by the first and second cartridges, based on accessing cartridge information from at least one of the first and second cartridges.

In some example embodiments, the control circuitry may be configured to establish a first communication link with a first storage device in the first cartridge. The control circuitry may be configured to access cartridge information from the first storage device via the first communication link, the cartridge information being associated with the first cartridge.

In some example embodiments, the cartridge information includes at least one of information uniquely identifying one or more elements of a dispersion generator included in the first cartridge, information indicating a dispersion generator "type" of a dispersion generator included in the first cartridge, information associated with a formulation held in the first cartridge, and a particular activation sequence associated with a dispersion generator included in the first cartridge.

In some example embodiments, the control circuitry may be configured to independently control dispersion generation by the first and second cartridges based on independent control of electrical power supplied from the power supply to the first and second cartridges via the first and second connectors.

In some example embodiments, the control circuitry may be configured to independently control the electrical power supplied to the first and second cartridges, such that electrical power is supplied to the first and second cartridges at different times.

In some example embodiments, the control circuitry may be configured to independently control the electrical power supplied to the first and second cartridges, such that electrical power is supplied to alternate cartridges of the first and second cartridges in response to successive vaping command signals.

In some example embodiments, the control circuitry may be configured to independently control the electrical power supplied to the first and second cartridges, such that a dispersion generator included in the second cartridge generates a dispersion based on heat generated by a dispersion generator included in the first cartridge.

In some example embodiments, the first and second cartridges may include at least one atomizer assembly and at least one vaporizer assembly, the atomizer assembly being configured to generate an aerosol via applying mechanical force to a pre-aerosol formulation, the vaporizer assembly being configured to generate a vapor via heating a pre-vapor formulation.

In some example embodiments, the power supply includes a rechargeable battery.

According to some example embodiments, a method may include independently controlling dispersion generation by first and second cartridges electrically coupled to a power supply of a base. The independently controlling may include establishing a first communication link with a first storage device in the first cartridge via the first connector, accessing cartridge information associated with the first cartridge from the first storage device via the first communication link, and independently controlling electrical power supplied to at least one of the first and second cartridges based on the accessed cartridge information.

In some example embodiments, the method may include independently controlling the electrical power supplied to at least one of the first and second connectors, such that electrical power is supplied to the first and second cartridges at different times.

In some example embodiments, the method may include independently controlling the electrical power supplied to at least one of the first and second connectors, such that electrical power is supplied to alternate cartridges of the first and second cartridges in response to successive vaping command signals.

In some example embodiments, the method may include independently controlling the electrical power supplied to at least one of the first and second connectors, such that a dispersion generator included in the second cartridge generates a dispersion based on heat generated by a dispersion generator included in the first cartridge.

In some example embodiments, the first and second cartridges may include at least one atomizer assembly and at least one vaporizer assembly, the atomizer assembly being configured to generate an aerosol via applying mechanical force to a pre-aerosol formulation, the vaporizer assembly being configured to generate a vapor via heating a pre-vapor formulation.

According to some example embodiments, a base may include a power supply, at least first and second connectors, control circuitry, and a cover configured to establish a removable enclosure of the first and second connectors. The power supply may be configured to supply electrical power. The first and second connectors may be configured to electrically couple separate, respective first and second cartridges to the power supply. The control circuitry may be configured to independently control dispersion generation by the first and second cartridges, based on cartridge information accessed through at least one of the first and second connectors.

According to some example embodiments, a base may include a power supply configured to supply electrical power and a cartridge holder. The cartridge holder may be configured to removably electrically couple at least first and second cartridges to the power supply. The cartridge holder may include at least first and second connectors electrically coupled to the power supply, the first and second connectors being configured to removably connect with separate, respective connectors of the first and second cartridges, the first connector being restricted from directly coupling with the second cartridge, the second connector being restricted from directly coupling with the first cartridge.

In some example embodiments, the base may include a divider coupled to the cartridge holder, the divider being configured to partition the first and second connectors from each other, such that the first and second cartridges generate separate, respective first and second dispersions in isolation from each other.

In some example embodiments, the first and second cartridges may include at least one atomizer assembly and at least one vaporizer assembly, the atomizer assembly being configured to generate an aerosol via applying mechanical force to a pre-aerosol formulation, the vaporizer assembly being configured to generate a vapor via heating a pre-vapor formulation.

In some example embodiments, the cartridge holder may include first and second slots configured to structurally support the first and second cartridges coupled to the first and second connectors, the first slot being restricted from holding the second cartridge, the second slot being restricted from holding the first cartridge.

In some example embodiments, the base may include control circuitry configured to independently control electrical power supplied from the power supply to the first and second connectors, based on cartridge information accessed through at least one of the first and second connectors.

In some example embodiments, the control circuitry may be configured to establish a first communication link with a first storage device in the first cartridge via the first connector. The control circuitry may be configured to access cartridge information from the first storage device via the first communication link, the cartridge information being associated with the first cartridge.

In some example embodiments, the cartridge information may include at least one of information uniquely identifying one or more elements of a dispersion generator included in the first cartridge, information indicating a dispersion generator "type" of a dispersion generator included in the first cartridge, information associated with a formulation held in the first cartridge, and a particular activation sequence associated with a dispersion generator included in the first cartridge.

In some example embodiments, the power supply may include a rechargeable battery.

According to some example embodiments, an e-vaping device may include a power supply configured to supply electrical power, a cartridge holder including at least first and second connectors electrically coupled to the power supply, and at least first and second cartridges removably coupled to separate, respective connectors of the first and second connectors such that the first and second cartridges are removably electrically coupled to the power supply. The first connector may be restricted from directly coupling with the second cartridge, and the second connector may be restricted from directly coupling with the first cartridge.

In some example embodiments, the e-vaping device may include a divider coupled to the cartridge holder, the divider partitioning the first and second cartridges from each other, such that the first and second cartridges are configured to generate separate, respective first and second dispersions in isolation from each other.

In some example embodiments, the first and second cartridges may include at least one atomizer assembly and at least one vaporizer assembly, the atomizer assembly being configured to generate an aerosol via applying mechanical force to a pre-aerosol formulation, the vaporizer assembly being configured to generate a vapor via heating a pre-vapor formulation.

In some example embodiments, the cartridge holder may include first and second slots configured to structurally support the first and second cartridges, the first slot being restricted from holding the second cartridge, the second slot being restricted from holding the first cartridge.

In some example embodiments, the e-vaping device may include control circuitry configured to independently control electrical power supplied from the power supply to the first and second connectors, based on cartridge information accessed through at least one of the first and second connectors.

In some example embodiments, the control circuitry may be configured to establish a first communication link with a first storage device in the first cartridge via the first connector. The control circuitry may be configured to access cartridge information from the first storage device via the first communication link, the cartridge information being associated with the first cartridge.

In some example embodiments, the cartridge information may include at least one of information uniquely identifying one or more elements of a dispersion generator included in the first cartridge, information indicating a dispersion generator "type" of a dispersion generator included in the first cartridge, information associated with a formulation held in the first cartridge, and a particular activation sequence associated with a dispersion generator included in the first cartridge.

In some example embodiments, the power supply may include a rechargeable battery.

According to some example embodiments, a base may include a power supply configured to supply electrical power, a cover configured to establish a removable enclosure of the first and second connectors, and a cartridge holder configured to removably electrically couple at least first and second cartridges to the power supply. The cartridge holder may include at least first and second connectors electrically coupled to the power supply, the first and second connectors being configured to removably connect with separate, respective connectors of the first and second cartridges, the first connector being restricted from directly coupling with the second cartridge, and the second connector being restricted from directly coupling with the first cartridge.

In some example embodiments, the base may include a divider coupled to the cartridge holder, the divider being configured to partition the first and second connectors from each other, such that the first and second cartridges generate separate, respective first and second dispersions in isolation from each other.

In some example embodiments, the first and second cartridges may include at least one atomizer assembly and at least one vaporizer assembly, the atomizer assembly being configured to generate an aerosol via applying mechanical force to a pre-aerosol formulation, the vaporizer assembly being configured to generate a vapor via heating a pre-vapor formulation.

In some example embodiments, the cartridge holder may include first and second slots configured to structurally support the first and second cartridges coupled to the first and second connectors, the first slot being restricted from holding the second cartridge, the second slot being restricted from holding the first cartridge.

In some example embodiments, the base may include control circuitry configured to independently control electrical power supplied from the power supply to the first and second connectors, based on cartridge information accessed through at least one of the first and second connectors.

In some example embodiments, the control circuitry may be configured to establish a first communication link with a first storage device in the first cartridge via the first connector. The control circuitry may be configured to access cartridge information from the first storage device via the first communication link, the cartridge information being associated with the first cartridge.

In some example embodiments, the cartridge information may include at least one of information uniquely identifying one or more elements of a dispersion generator included in the first cartridge, information indicating a dispersion generator "type" of a dispersion generator included in the first cartridge, information associated with a formulation held in the first cartridge, and a particular activation sequence associated with a dispersion generator included in the first cartridge.

In some example embodiments, the power supply may include a rechargeable battery.

Some example embodiments relate to a cartridge of an electronic vaping device.

In some example embodiments, a cartridge of an electronic vaping device includes a vaporizer assembly and an atomizer assembly. The vaporizer assembly is configured to produce a vapor. The vaporizer assembly includes a first tank configured to store a pre-vapor formulation, and a heater configured to heat the pre-vapor formulation and form a vapor. The atomizer assembly is configured to produce an aerosol. The atomizer assembly includes a second tank configured to store a pre-aerosol formulation, and an atomizer configured to atomize the pre-aerosol formulation and form the aerosol without heat.

In some example embodiments, the vaporizer assembly may include a tube having an inlet and an outlet. The inlet is in communication with the pre-vapor formulation. A portion of the tube forms the heater. The tube may have an internal diameter of about 0.05 to 0.4 mm and a length of about 5 mm to about 72 mm. The tube may include one of a stainless steel tube and a non-metallic tube. The tube may have a constriction adjacent the outlet of the tube. The tube may include at least one bend therein.

In some example embodiments, the first tank is pressurized. The first tank may include a first valve between an outlet of the first tank and the inlet of the tube. The first valve may be one of a solenoid valve and a push-button valve.

In some example embodiments, the second tank may include a second valve at an outlet of the second tank. The second valve may be one of a solenoid valve and a push-button valve.

In some example embodiments, the atomizer includes at least one of a piezoelectric element and a pressurization arrangement. The atomizer is configured to produce an aerosol without heating the pre-aerosol formulation.

In some example embodiments, the pressurization arrangement includes a spring and a piston configured to apply pressure to the second tank. The second tank may have a flexible wall.

In some example embodiments, the pressurization arrangement includes a container housing the second tank, and a constant pressure fluid in the container and surrounding the second tank so as to apply pressure to the second tank. The second tank may have a flexible wall. The constant pressure fluid may be 1,1,1,2-tetrafluoroethane.

In some example embodiments, the pressurization arrangement may include a capsule of carbon dioxide, and a dual piston cylinder between the second tank and the capsule of carbon dioxide. The capsule of carbon dioxide applies pressure to the pre-aerosol formulation in the second tank. The second tank has a flexible wall. The dual piston cylinder reduces pressure on the second tank.

In some example embodiments, the pre-vapor formulation and the pre-aerosol formulation have different viscosities at room temperature.

In some example embodiments, one of the pre-vapor formulation and the pre-aerosol formulation includes flavor material and another one of the pre-vapor formulation and the pre-aerosol formulation includes nicotine.

In some example embodiments, the cartridge may also include a mixing chamber downstream of the vaporizer assembly and the atomizer assembly, and at least one air inlet configured to provide air to the mixing chamber.

In some example embodiments, the cartridge may include a window in an outer housing of the cartridge. At least one of the first tank and the second tank is visible through the window.

In some example embodiments, the vapor has a first particle size distribution and the aerosol has a second particle size distribution. A mean particle size of the second particle size distribution is larger than a mean particle size of the first particle size distribution.

Some example embodiments relate to an electronic vaping device.

In some example embodiments, an electronic vaping device includes a cartridge and a second section. The cartridge includes a vaporizer assembly and an atomizer assembly. The vaporizer assembly is configured to produce a vapor. The vaporizer assembly includes a first tank configured to store a pre-vapor formulation, and a heater configured to heat the pre-vapor formulation and form a vapor. The atomizer assembly is configured to produce an aerosol. The atomizer assembly includes a second tank configured to store a pre-aerosol formulation, and an atomizer configured to atomize the pre-aerosol formulation and form the aerosol without heating the pre-aerosol formulation. The second section includes a power supply configured to supply power to the heater.

In some example embodiments, the vaporizer assembly includes a tube having an inlet and an outlet. The inlet is in communication with the pre-vapor formulation. A portion of the tube forms the heater.

In some example embodiments, the atomizer includes at least one of a piezoelectric element and a pressurization arrangement. The atomizer is configured to produce the aerosol without heating the pre-aerosol formulation.

In some example embodiments, the electronic vaping device also includes a first valve between an outlet of the first tank and the inlet of the tube. The first valve is one of a solenoid valve and a push-button valve. The electronic vaping device also includes a second valve at an outlet of the second tank. The second valve is one of a solenoid valve and a push-button valve. The first valve and the second valve may be electrically operated valves. The electronic vaping device may further include a pressure switch configured to send a signal to open the first valve and the second valve.

In some example embodiments, the vapor has a first particle size distribution and the aerosol has a second particle size distribution. A mean particle size of the second particle size distribution is larger than a mean particle size of the first particle size distribution.

BRIEF DESCRIPTION OF THE DRAWINGS

The various features and advantages of the non-limiting embodiments described herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION OF EXAMPLE EMBODIMENTS

Figure 1A:
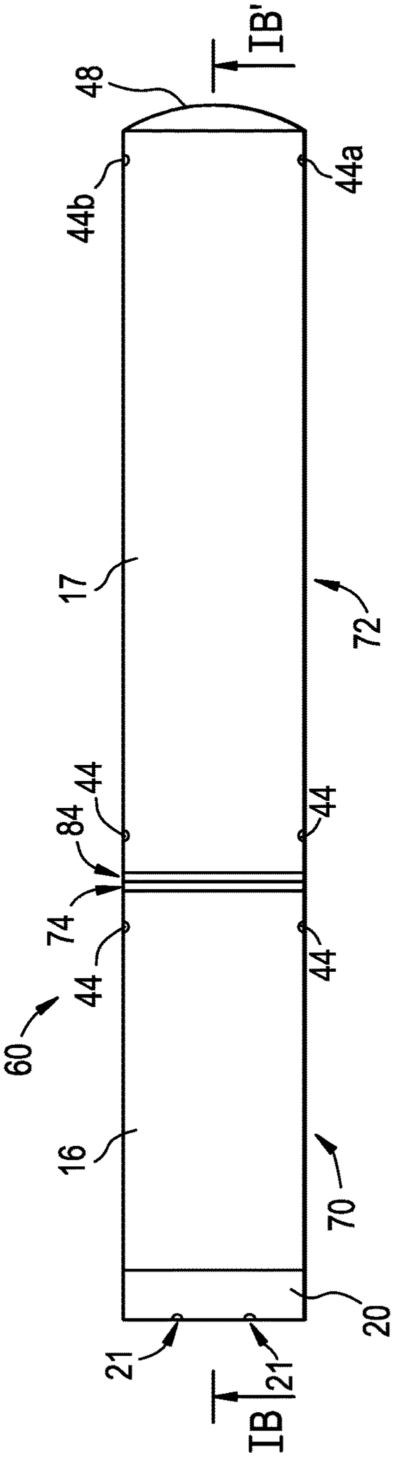
FIG. 1A is a side view of an e-vaping device according to some example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, elements, regions, layers and/or sections, these elements, elements, regions, layers, and/or sections should not be limited by these terms. These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Figure 1B:
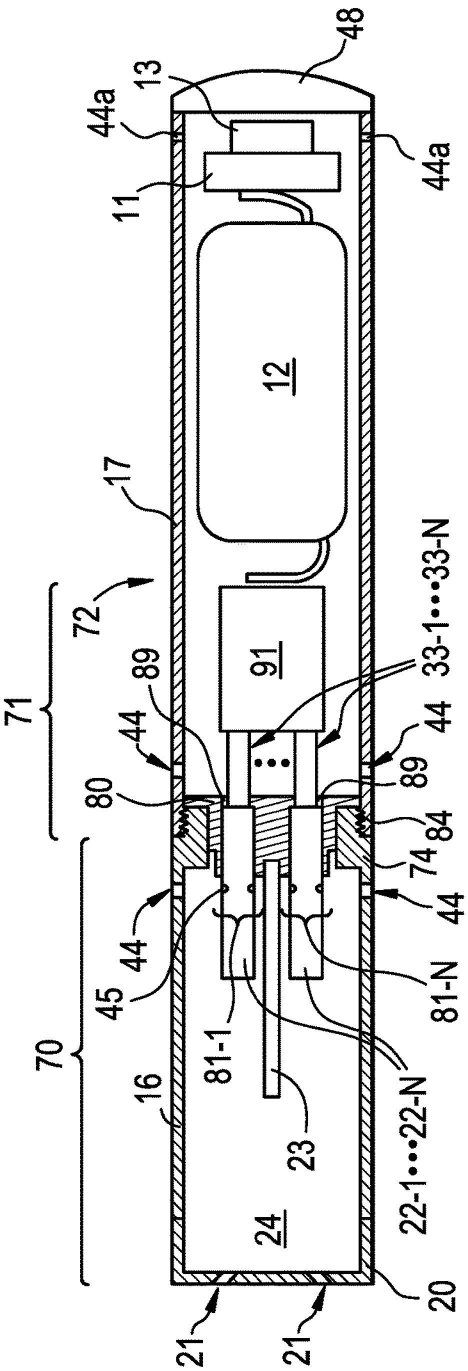
FIG. 1B is a cross-sectional view along line IB-IB' of the e-vaping device of FIG. 1A.

FIG. 1A is a side view of an e-vaping device 60 according to some example embodiments. FIG. 1B is a cross-sectional view along line IB-IB' of the e-vaping device 60 of FIG. 1A. The e-vaping device 60 may include one or more of the features set forth in U.S. Patent Application Publication No. 2013/0192623 to Tucker et al. filed Jan. 31, 2013 and U.S. Patent Application Publication No. 2013/0192619 to Tucker et al. filed Jan. 14, 2013, the entire contents of each of which are incorporated herein by reference thereto. As used herein, the term "e-vaping device" is inclusive of all types of electronic vaping devices, regardless of form, size or shape.

Referring to FIG. 1A and FIG. 1B, an e-vaping device 60 may include a cover (or first section) 70, a reusable base (or second section) 71, and one or more cartridges 22-1 to 22-N, where "N" is a positive integer. In some example embodiments, "N" has a value of at least two (2). The cover 70 and base 71 may be part of an e-vaping device kit. An e-vaping device kit may be a package that includes at least one of a cartridge 22-1 to 22-N, a cover 70, a base 71, and a power supply charger configured to couple with the base 71 and supply electrical power to a power supply 12 included therein. As shown in FIG. 1B, base 71 is configured to couple with one or more cartridges 22-1 to 22-N to support vaping. In some example embodiments, a base for an e-vaping device includes the base 71 and excludes the cover 70.

The base 71 includes a power supply section 72 and a cartridge holder 80. The cartridge holder 80 is coupled to the power supply section 72. The cover 70 and base 71 are coupled together at complementary interfaces 74, 84. In some example embodiments, interface 84 is included in the cartridge holder 80, and the cover 70 and cartridge holder 80 may be coupled together via interfaces 74, 84. In some example embodiments, interface 84 is included in the power supply section 72, and the cover 70 and power supply section 72 may be coupled together via interfaces 74, 84.

In some example embodiments, the interfaces 74, 84 are threaded connectors. It should be appreciated that an interface 74, 84 may be any type of connector, including, without limitation, a snug-fit, detent, clamp, bayonet, and/or clasp.

Referring to FIG. 1A and FIG. 1B, the e-vaping device 60 includes multiple separate cartridges 22-1 to 22-N. As used herein, "N" is a positive integer having a value of at least one (1). In some example embodiments, "N" has a value of at least two (2), such that the base 71 is configured to couple with at least two cartridges 22-1 to 22-N. Cartridges 22-1 to 22-N are described in further detail below with regard to FIG. 3A, FIG. 3B, and FIG. 3C.

In some example embodiments, each separate cartridge of cartridges 22-1 to 22-N includes one or more dispersion generators. In the example embodiment shown in FIG. 1B, the separate cartridges 22-1 to 22-N include separate ones of at least first and second dispersion generators such that cartridge 22-1 includes a first dispersion generator and cartridge 22-N includes a second dispersion generator. In some example embodiments, and as described further below, at least first and second cartridges 22-1 to 22-N include different dispersion generators configured to generate different dispersions.

Dispersion generators, as described herein, may include different types of dispersion generators configured to generate different types of dispersions. A dispersion may include at least one of a vapor and an aerosol. A vapor is a dispersion that is generated through application of heat to a pre-dispersion formulation. A pre-dispersion formulation to which heat may be applied to generate a vapor may be referred to as a pre-vapor formulation. An aerosol is a dispersion that is generated through application of mechanical force to a pre-dispersion formulation. A pre-dispersion formulation to which mechanical force may be applied to generate an aerosol may be referred to as a pre-aerosol formulation.

In some example embodiments, a dispersion generator may be a vaporizer assembly or an atomizer assembly. A vaporizer assembly may generate a dispersion that is a vapor. A vaporizer assembly may generate the vapor via heating a pre-vapor formulation to vaporize at least a portion of the pre-vapor formulation. An atomizer assembly may generate a dispersion that is an aerosol via applying a mechanical force to a pre-dispersion formulation. An atomizer assembly may include one or more mechanical elements configured to apply the mechanical force. For example, an atomizer assembly may include a pressurized tank holding a pre-aerosol formulation, and the atomizer assembly may further include a mechanical element that includes one or more of a valve, pump, sprayer, some combination thereof, or the like.

One or more portions of the atomizer assembly, including the mechanical element may exert a mechanical force on the pre-aerosol formulation to generate a dispersion that is an aerosol. For example, an atomizer assembly may be configured to generate an aerosol via one or more of releasing a pressurized pre-aerosol formulation into a lower-pressure environment, spraying pre-aerosol formulation particles, evaporating volatile pre-aerosol formulations into an environment, some combination thereof, etc.

Different dispersion generators may include different formulations. For example, the first and second dispersion generators may be vaporizer assemblies configured to generate first and second vapors by heating different pre-vapor formulations.

In some example embodiments, a dispersion generator included in at least one of cartridges 22-1 to 22-N is configured to generate a dispersion that is substantially free of flavorants. Another dispersion generator included in another at least one of cartridges 22-1 to 22-N may be configured to generate a separate dispersion that includes one or more flavorants. The separate dispersions generated by the dispersion generators in the separate cartridges 22-1 to 22-N may combine to generate a flavored dispersion.

In some example embodiments, one or more cartridges 22-1 to 22-N may include one or more air inlet ports 45. Air received into an interior of the e-vaping device via one or more air inlet ports 44 may further be received into an interior of the one or more cartridges 22-1 to 22-N via the one or more air inlet ports 45. In some example embodiments, one or more cartridges 22-1 to 22-N include one or more openings (not shown in FIG. 1A and FIG. 1B) via which one or more of air, dispersions, etc. may exit the one or more cartridges 22-1 to 22-N.

Still referring to FIG. 1A and FIG. 1B, the base 71 includes a cartridge holder 80. The cartridge holder 80, described in further detail below with regard to FIG. 2A, FIG. 2B, and FIG. 2C, includes connectors 33-1 to 33-N and slots 81-1 to 81-N. The cartridge holder 80 is configured to removably couple with one or more cartridges 22-1 to 22-N via connectors 33-1 to 33-N, such that the one or more cartridges 22-1 to 22-N are removably electrically coupled with the power supply 12.

The connectors 33-1 to 33-N are configured to be coupled to separate cartridges 22-1 to 22-N and are further coupled to the connector element 91 of the power supply section 72 that is discussed further below. As discussed below, the connector element 91 is coupled to a power supply 12 in the power supply section 72. Thus, the connectors 33-1 to 33-N may be electrically coupled to the power supply 12 in the power supply section 72. Each of connectors 33-1 to 33-N may supply at least a portion of the electrical power from the power supply 12 to a respective coupled one of cartridges 22-1 to 22-N.

The separate slots 81-1 to 81-N may be configured to receive and structurally support separate cartridges 22-1 to 22-N in the e-vaping device 60. The slots 81-1 to 81-N may be configured to hold separate, respective cartridges 22-1 to 22-N in contact with separate, respective connectors 33-1 to 33-N. In some example embodiments, one or more connectors 33-1 to 33-N are included in one or more slots 81-1 to 81-N. At least one of slots 81-1 to 81-N may hold at least one of cartridges 22-1 to 22-N inserted thereto in contact with at least one of connectors 33-1 to 33-N included in the at least one of slots 81-1 to 81-N. In some example embodiments, at least one of slots 81-1 to 81-N is configured to hold an inserted at least one of cartridges 22-1 to 22-N in contact with at least one of connectors 33-1 to 33-N via establishing a friction fit or other connection between the at least one of slots 81-1 to 81-N and the inserted at least one of cartridges 22-1 to 22-N.

In the example embodiment of FIG. 1B, the connectors 33-1 to 33-N are configured to electrically couple the cartridges 22-1 to 22-N inserted into respective slots 81-1 to 81-N with the power supply 12 included in the base 71 via connector element 91. At least one of the connectors 33-1 to 33-N may be configured to electrically couple at least one dispersion generator included in at least one of the cartridges 22-1 to 22-N with the power supply 12. At least one of the connectors 33-1 to 33-N may be directly coupled, connected, etc. to a given dispersion generator included in a given cartridge of cartridges 22-1 to 22-N via directly coupling, connecting, etc. with a connector of the given cartridge of cartridges 22-1 to 22-N.

When the cartridge holder 80 is configured to removably couple with multiple separate cartridges 22-1 to 22-N, the cartridge holder 80 may enable multiple cartridges 22-1 to 22-N to be removably installed in the e-vaping device 60 at any given time. One or more cartridges 22-1 to 22-N may be individually or collectively added, removed, swapped, replaced, etc. with regard to the base 71 as desired. For example, a given one of cartridges 22-1 to 22-N configured to generate a particular dispersion having a first flavor may be decoupled from one of connectors 33-1 to 33-N and replaced with another one of cartridges 22-1 to 22-N that is configured to generate a different dispersion having a different flavor.

As a result, because the cartridge holder 80 may removably couple with multiple cartridges 22-1 to 22-N, the cartridge holder 80 enables variety and customization of the sensory experience provided during vaping.

In some example embodiments, at least two separate dispersions generated by at least two separate dispersion generators included in separate ones of at least two separate cartridges 22-1 to 22-N may combine to generate a dispersion with a combination of flavors. In some example embodiments, at least one of an e-vaping device 60 and a base 71 is configured to enable manual coupling of various different cartridges 22-1 to 22-N to the cartridge holder 80 to configure the at least one of an e-vaping device 60 and a base 71 to generate dispersions with various manually-selected combinations of flavors.

In some example embodiments, one or more of the cartridges 22-1 to 22-N may be replaceable from base 71. In other words, once one of the formulations of one of the cartridges 22-1 to 22-N is depleted, only the cartridge of cartridges 22-1 to 22-N need be replaced. The cartridges 22-1 to 22-N may be interchangeably coupled with the connectors 33-1 to 33-N. At least one of cartridges 22-1 to 22-N may be swapped for another at least one of cartridges 22-1 to 22-N. An alternate arrangement may include an example embodiment where the entire e-vaping device 60 may be disposed once one of the formulations is depleted.

Still referring to FIG. 1A and FIG. 1B, the e-vaping device 60 includes a cover 70 that may be removably coupled to one or more of the cartridge holder 80 or the power supply section 72 to establish a removable enclosure of cartridges 22-1 to 22-N coupled to the cartridge holder 80. The cover 70 may be configured to establish a removable enclosure of the connectors 33-1 to 33-N, such that the cover 70 may establish a removable enclosure of one or more cartridges 22-1 to 22-N when the one or more cartridges 22-1 to 22-N are coupled to one or more of the connectors 33-1 to 33-N.

The cover 70 includes an outer housing 16, an outlet end insert 20 at an outlet end of the outer housing 16, and an interface 74 at a tip end of the outer housing 16. The outer housing 16 extends in a longitudinal direction. The outer housing 16 may have a generally cylindrical cross-section. In some example embodiments, the outer housing 16 may have a generally triangular cross-section along the cover 70. In some example embodiments, the outer housing 16 may have a greater circumference or dimensions at a tip end than at an outlet end of the e-vaping device 60.

The outlet end insert 20 is positioned at an outlet end of the cover 70. The outlet end insert 20 includes at least two outlet ports 21, which may be located on-axis and/or off-axis from the longitudinal axis of the e-vaping device 60. The outlet ports 21 may be angled outwardly in relation to the longitudinal axis of the e-vaping device 60. The outlet ports 21 may be substantially uniformly distributed about the perimeter of the outlet end insert 20 so as to substantially uniformly distribute dispersion during vaping. Thus, as the dispersion is drawn through the outlet ports 21, the dispersion may move in different directions.

The cartridge holder 80 may include a divider 23 configured to partition a portion of the outer housing 16 interior when the cover 70 is coupled to the base 71. In some example embodiments, the divider 23 partitions the connectors 33-1 to 33-N, such that the separate cartridges 22-1 to 22-N coupled to the separate connectors 33-1 to 33-N may generate separate dispersions in isolation from each other. In some example embodiments, the divider 23 is coupled to the outer housing 16 instead of being coupled to the cartridge holder 80, and the divider 23 partitions the connectors 33-1 to 33-N based on the cover 70 being coupled to the base 71.

The cover 70 may define an enclosure that includes a passage 24 (also referred to as a mixing chamber) within the outer housing 16 interior. Dispersions generated by the separate dispersion generators included in the separate, respective cartridges 22-1 to 22-N may pass through the passage 24 to the outlet ports 21 of the outlet end insert 20 to exit the e-vaping device 60 during vaping. The dispersions passing through the passage 24 may combine in a portion of the passage 24 to generate a combined dispersion. Thus, a combined dispersion may be generated by combining separate dispersions, where the separate dispersions are generated separately by separate dispersion generators included in separate cartridges 22-1 to 22-N.

In some example embodiments, combining the separate dispersions in passage 24 mitigates chemical reactions between the separate elements of the separate dispersions. For example, combining the dispersions in passage 24, downstream from the cartridges 22-1 to 22-N, may result in the dispersions cooling from an initial temperature. Because the dispersions may combine in passage 24, the dispersions may be cooler than when the dispersions are initially generated when the dispersions pass through passage 24. Thus, a probability of chemical reactions between the dispersions may be reduced, relative to a probability of chemical reactions between the dispersions when the dispersions are generated.

In some example embodiments, combining the separate dispersions in passage 24 mitigates a risk of the formulations held by the separate cartridges 22-1 to 22-N mixing prior to dispersion generation, thereby mitigating a risk of chemical reactions between the separate formulations.

Still referring to FIG. 1A and FIG. 1B, the e-vaping device 60 includes one or more air inlet ports 44. In the example embodiment shown in FIG. 1A and FIG. 1B, air inlet ports 44 are included in both the outer housing 16 of the cover 70 and the outer housing 17 of the base 71. In some example embodiments, the e-vaping device 60 may include one or more air inlet ports 44 restricted to the outer housing 16 of the cover 70. In some example embodiments, the e-vaping device may include one or more air inlet ports 44 restricted to the outer housing 17 of the base 71.

It should be appreciated that more than two air inlet ports 44 may be included in at least one of the outer housing 16 and the outer housing 17. Alternatively, a single air inlet port 44 may be included in at least one of the outer housing 16 and the outer housing 17. Such arrangement may also reinforce the area of air inlet ports 44 to facilitate precise drilling of the air inlet ports 44. In some example embodiments, one or more air inlet ports 44 may be provided in the interface 74.

In some example embodiments, at least one air inlet port 44 may be formed in the outer housing 16, adjacent to the interface 74 to minimize the probability of an adult vaper's fingers occluding one of the ports and to control the resistance-to-draw (RTD) during vaping. In some example embodiments, the air inlet ports 44 may be machined into the outer housing 16 with precision tooling such that their diameters are closely controlled and replicated from one e-vaping device 60 to the next during manufacture.

In some example embodiments, one or more air inlet ports 44 may be drilled with carbide drill bits or other high-precision tools and/or techniques. In yet a further example embodiment, the outer housing 16 may be formed of metal or metal alloys such that the size and shape of the air inlet ports 44 may not be altered during manufacturing operations, packaging, and vaping. Thus, the air inlet ports 44 may provide consistent RTD. In yet a further example embodiment, the air inlet ports 44 may be sized and configured such that the e-vaping device 60 has a RTD in the range of from about 60 mm $H_2O$ to about 150 mm $H_2O$.

In some example embodiments, the cartridge holder 80 includes one or more air inlet ports 89. The air inlet ports 89 may be configured to establish one or more air passages between an interior of the base 71 and at least one of slots 81-1 to 81-N. In the example embodiment shown in FIG. 1B, the cartridge holder 80 includes separate air inlet ports 89 that are each configured to direct air into a separate slot of slots 81-1 to 81-N. Air drawn into the interior of the base 71 through one or more air inlet ports 44 formed on the outer housing 17 may be drawn into one or more slots 81-1 to 81-N through one or more air inlet ports 89 included in the cartridge holder 80.

If and/or when an air inlet port 89 establishes an air passage between the interior of the base 71 and at least one slot 81-1 to 81-N in which at least one cartridge 22-1 to 22-N is located, air drawn through the air inlet port 89 from the interior of the base 71 may be drawn into the at least one of the cartridges 22-1 to 22-N via one or more air inlet ports 45.

Still referring to FIG. 1A and FIG. 1B, the base 71 includes a power supply section 72. The power supply section 72 includes a sensor 13 responsive to air drawn into the power supply section 72 via an air inlet port **44*a* adjacent to a free end or tip end of the e-vaping device 60, at least one power supply 12, activation light 48, connector element 91, and control circuitry 11. The sensor 13 may include one or more various types of sensors, including at least one of a negative pressure sensor, a button interface sensor, and a microelectromechanical system (MEMS) sensor. The power supply 12 may include a battery. The battery may be a rechargeable battery. Connector element 91** may include one or more of a cathode connector element and an anode connector element.

Upon completing the connection between the cartridge holder 80 and the one or more cartridges 22-1 to 22-N, the connectors 33-1 to 33-N may electrically couple at least one power supply 12 with the one or more cartridges 22-1 to 22-N. Electrical power may be supplied from the power supply 12 to the electrically coupled cartridges 22-1 to 22-N upon actuation of the sensor 13. The sensor 13 may generate a vaping command signal, and the electrical power may be supplied based on the signal. Air is drawn primarily into the cover 70 through one or more air inlet ports 44, which may be located along the outer housing 16, 17 of the cover 70 and base 71 or at the coupled interfaces 74, 84.

The power supply 12 may be a Lithium-ion battery or one of its variants, for example a Lithium-ion polymer battery. Alternatively, the power supply 12 may be a nickel-metal hydride battery, a nickel cadmium battery, a lithium-manganese battery, a lithium-cobalt battery or a fuel cell. The e-vaping device 60 may be usable by an adult vaper until the energy in the power supply 12 is depleted or in the case of a lithium polymer battery, a minimum voltage cut-off level is achieved.

Further, the power supply 12 may be rechargeable and may include circuitry configured to allow the battery to be chargeable by an external charging device. To recharge the e-vaping device 60, a Uniform Serial Bus (USB) charger or other suitable charger assembly may be used.

The sensor 13 may be configured to sense an air pressure drop and initiate application of voltage from the power supply 12 to one or more of the cartridges 22-1 to 22-N.

The activation light 48 may be configured to glow when one or more of the dispersion generators are activated to generate one or more dispersions. The activation light 48 may include a light emitting diode (LED). Moreover, the activation light 48 may be arranged to be visible to an adult vaper during vaping. In addition, the activation light 48 may be utilized for e-vaping system diagnostics or to indicate that recharging is in progress. The activation light 48 may also be configured such that the adult vaper may activate and/or deactivate the activation light 48 for privacy. As shown in FIG. 1A and FIG. 1B, the heater activation light 48 may be located on the tip end of the e-vaping device 60. In some example embodiments, the heater activation light 48 may be located on a side portion of the outer housing 17.

In addition, the at least one air inlet port **44*a* is located adjacent to the sensor 13, such that the sensor 13 may sense air flow indicative of an adult vaper initiating vaping, and activate the power supply 12 and the activation light 48 to indicate that the one or more dispersion generators included in one or more cartridges 22-1 to 22-N that are electrically coupled to the power supply section 72** is working.

Further, the control circuitry 11 may independently control the supply of electrical power from the power supply 12 to one or more of the cartridges 22-1 to 22-N responsive to the sensor 13. In some example embodiments, the control circuitry 11 may include a maximum, time-period limiter. In some example embodiments, the control circuitry 11 may include a manually operable switch for an adult vaper to initiate vaping. The time-period of the electric current supply to a cartridge of cartridges 22-1 to 22-N may be pre-set depending on the amount of dispersion desired to be generated. In some example embodiments, the control circuitry 11 may control the supply of electrical power to a dispersion generator included in a cartridge of cartridges 22-1 to 22-N as long as the sensor 13 detects a pressure drop.

To control the supply of electrical power to at least one of the cartridges 22-1 to 22-N, the control circuitry 11 may execute one or more instances of computer-executable code. The control circuitry 11 may include a processor and a memory. The memory may be a computer-readable storage medium storing computer-executable code.

The control circuitry 11 may include processing circuitry including, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. In some example embodiments, the control circuitry 11 may be at least one of an application-specific integrated circuit (ASIC) and an ASIC chip.

The control circuitry 11 may be configured as a special purpose machine by executing computer-readable program code stored on a storage device. The program code may include program or computer-readable instructions, software elements, software modules, data files, data structures, and/or the like, capable of being implemented by one or more hardware devices, such as one or more of the control circuitry mentioned above. Examples of program code include both machine code produced by a compiler and higher level program code that is executed using an interpreter.

The control circuitry 11 may include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a USB flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

In some example embodiments, the control circuitry 11 controls the supply of electrical power to one or more of the connectors 33-1 to 33-N of the cartridge holder 80 responsive to the sensor 13, where the separate connectors 33-1 to 33-N are coupled to the separate, respective cartridges 22-1 to 22-N in which separate dispersion generators are included. The control circuitry 11 may independently adjustably control one or more aspects of the electrical power supplied to respective dispersion generators included in one or more of the respective cartridges 22-1 to 22-N via the respective connectors 33-1 to 33-N. In some example embodiments, the control circuitry 11 selectively controls the supply of electrical power to a selected one or more of the cartridges 22-1 to 22-N, such that at least one dispersion generator included in one or more cartridges 22-1 to 22-N does not generate a dispersion. In some example embodiments, the control circuitry 11 controls the supply of electrical power to the cartridges 22-1 to 22-N, so that the dispersion generators included in the separate cartridges 22-1 to 22-N generate separate dispersions at different times. The control circuitry 11 may control the supply of electrical power to control the generation and delivery of dispersions. Such control may include extending the duration of dispersion generation by one or more dispersion generators.

In some example embodiments, the control circuitry 11 may independently control dispersion generation by separate dispersion generators included in separate cartridges 22-1 to 22-N. For example, the control circuitry 11 may independently control the supply of electrical power to the separate cartridges 22-1 to 22-N via independent control of the supply of electrical power to one or more of the respective connectors 33-1 to 33-N.

In some example embodiments, the control circuity 11 may independently control one or more aspects of electrical power supplied to one or more separate cartridges 22-1 to 22-N to independently control dispersion generation by one or more dispersion generators included in the one or more separate cartridges 22-1 to 22-N. To control dispersion generation by a dispersion generator, the control circuitry 11 may execute one or more instances of computer-executable code. The control circuitry 11 may include a processor and a memory. The memory may be a computer-readable storage medium storing computer-executable code. The control circuitry 11 may be a special purpose machine configured to execute the computer-executable code to control dispersion generation by one or more dispersion generators.

In some example embodiments, a dispersion generator included in at least one of the cartridges 22-1 to 22-N is a vaporizer assembly that includes a reservoir, wick, and heater, and the control circuitry 11 may independently control vapor generation by the vaporizer assembly by controlling the supply of electrical power to the heater of the vaporizer assembly. The reservoir may hold one or more pre-vapor formulations. The wick may be coupled to the reservoir and may draw pre-vapor formulation from the reservoir. The heater may be coupled to the wick and may be configured to heat the drawn pre-vapor formulation to generate a vapor. The vaporizer assembly may include a connector to which the heater may be electrically coupled. Coupling the connector of the vaporizer assembly to at least one of connectors 33-1 to 33-N may electrically couple the heater to a power supply 12 via the at least one of connectors 33-1 to 33-N.

In some example embodiments, control circuitry 11 may selectively and independently control the supply of electrical power to separate cartridges to activate the separate dispersion generators included in the separate cartridges 22-1 to 22-N at different times. For example, the control circuitry 11 may activate one dispersion generator included in a cartridge 22-1 prior to activating another dispersion generator included in cartridge 22-N. In another example, the control circuitry 11 may maintain activation of one dispersion generator included in cartridge 22-1 subsequent to ending an activation of another dispersion generator included in cartridge 22-N.

In some example embodiments, the control circuitry 11 may control the supply of electrical power to activate separate dispersion generators included in separate cartridges 22-1 to 22-N at different times, such that separate cartridges 22-1 to 22-N generate separate dispersions during different, at least partially non-overlapping time periods. The control circuitry 11 may control the supply of electrical power to separate cartridges 22-1 to 22-N according to an activation sequence, so that separate dispersions are generated in the e-vaping device 60 in a particular sequence according to the activation sequence. Generating separate dispersions according to a particular sequence may provide a sequence of dispersions, one or more combined dispersions, etc. during vaping. Such a sequence of dispersions, one or more combined dispersions, etc. may enhance a sensory experience provided by an e-vaping device.

For example, the control circuitry 11 may control the supply of electrical power to cartridges 22-1 to 22-N to activate two separate dispersion generators respectively included in two separate cartridges 22-1 to 22-N in an alternating sequence, where the control circuitry 11 activates alternate dispersion generators in alternate cartridges 22-1 to 22-N according to successive vaping command signals. Successive vaping command signals may be generated by the sensor 13. As a result, the control circuitry 11 may switch between activating separate dispersion generators included in separate cartridges 22-1 to 22-N in an alternating sequence. Such an alternating activation of separate dispersion generators may enhance a sensory experience provided by an e-vaping device 60 during vaping. For example, by alternating between separate dispersion generators, the control circuitry 11 may mitigate a buildup of heat in any one dispersion generator due to successive vapings, thereby mitigating a risk of overheating of the e-vaping device 60, heat-induced chemical reactions involving multiple formulations, etc.

In some example embodiments, one or more cartridges 22-1 to 22-N include one or more storage devices (not shown in FIG. 1A and FIG. 1B), where the one or more storage devices store information associated with the respective one or more cartridges 22-1 to 22-N in which the one or more storage devices are included. The control circuitry 11 may access the information from the one or more storage devices. The control circuitry 11 may establish a communication link with one or more storage devices of one or more cartridges 22-1 to 22-N based on the one or more cartridges 22-1 to 22-N being electrically coupled to at least a portion of the base 71 via coupling with one or more connectors 33-1 to 33-N. In some example embodiments, electrically coupling a given cartridge of cartridges 22-1 to 22-N with the power supply 12 via coupling the given cartridge of cartridges 22-1 to 22-N to a connector of connectors 33-1 to 33-N includes communicatively coupling the control circuitry 11 with the cartridge of cartridges 22-1 to 22-N via the connector of connectors 33-1 to 33-N.

As discussed further below with reference to FIG. 3A, FIG. 3B, and FIG. 3C, the information stored on a storage device of a given cartridge of cartridges 22-1 to 22-N may include information indicating an identity of a dispersion generator included in the given cartridge 22, a dispersion generator "type" of the given dispersion generator (e.g., vaporizer assembly or atomizer assembly), particular properties of electrical power to supply to the given cartridge of cartridges 22-1 to 22-N to control dispersion generation by the dispersion generator included in the given cartridge 22, properties of one or more formulations held in the dispersion generator in the given cartridge 22, timing control parameters for supplying electrical power to the given cartridge 22, some combination thereof, or the like.

The control circuitry 11 may independently control dispersion generation by one or more of the dispersion generators included in one or more of the cartridges 22-1 to 22-N based on information accessed from one or more storage devices included in the one or more cartridges 22-1 to 22-N. between the control circuitry 11 and the one or more storage devices. The control circuitry 11 may, for example, control one or more parameters (e.g., at least one of voltage, current and time period of electrical power supplied) of electrical power supplied to a cartridge 22, thereby controlling dispersion generation by the dispersion generator included in the given cartridge 22, based on one or more portions of the information associated with one or more of the cartridges 22-1 to 22-N coupled to the base 71. The control circuitry 11 may independently control dispersion generation by one or more dispersion generators included in one or more cartridges 22-1 to 22-N according to a particular selected activation sequence, where the control circuitry 11 selects the particular activation sequence based on information associated with one or more dispersion generators included in one or more of the cartridges 22-1 to 22-N. For example, where the control circuitry 11 determines that dispersion generators included in multiple cartridges 22-1 to 22-N coupled to holder 80 are vaporizer assemblies, the control circuitry 11 may independently control the supply of electrical power to the vaporizer assemblies included in the cartridges 22-1 to 22-N, during vaping, so that the vaporizer assemblies generate vapors according to an activation sequence where the vaporizer assemblies generate vapors at different times. In another example, where the control circuitry 11 determines that dispersion generators included in multiple cartridges 22-1 to 22-N coupled to holder 80 are vaporizer assemblies holding a common pre-vapor formulation, the control circuitry 11 may independently control the supply of electrical power to the vaporizer assemblies, during successive vapings, so that alternate vaporizer assemblies generate vapors with each successive vaping command signal. Based on including control circuitry 11 that is configured to independently control dispersion generation by dispersion generators included in coupled cartridges 22-1 to 22-N based on associated information accessed from storage devices in one or more cartridges 22-1 to 22-N, a base 71 may provide an improved sensory experience.

As described herein, activating a dispersion generator included in a cartridge of cartridges 22-1 to 22-N may include causing the dispersion generator to generate a dispersion. Such activating may include, for example, supplying electrical power to a heater included in the dispersion generator to vaporize a pre-vapor formulation. Such activating may also include supplying electrical power to a sprayer assembly, valve assembly, etc. included in the dispersion generator to release a pre-dispersion formulation into an external environment.

When activated, a dispersion generator may operate to generate a dispersion for less than about 10 seconds. Thus, the power cycle (or maximum vaping length) may range in period from about 2 seconds to about 10 seconds (e.g., about 3 seconds to about 9 seconds, about 4 seconds to about 8 seconds or about 5 seconds to about 7 seconds).

As used herein, the term "flavorant" is used to describe a compound or combination of compounds that may provide flavor and/or aroma. In some example embodiments, a flavorant is configured to interact with at least one of an adult vaper orthonasal sensory receptor or an adult vaper retronasal sensory receptor. A flavorant may include one or more volatile flavor substances.

A flavorant may include one or more of a natural flavorant or an artificial ("synthetic") flavorant. In some example embodiments, a flavorant is one or more of tobacco flavor, menthol, wintergreen, peppermint, herb flavors, fruit flavors, nut flavors, liquor flavors, and combinations thereof. In some example embodiments, a flavorant is included in a botanical material. A botanical material may include material of one or more plants. A botanical material may include one or more herbs, spices, fruits, roots, leaves, grasses, or the like. For example, a botanical material may include orange rind material and sweetgrass material. In another example, a botanical material may include tobacco material.

In some example embodiments, the tobacco material may include material from any member of the genus *Nicotiana*. In some example embodiments, the tobacco material includes a blend of two or more different tobacco varieties. Examples of suitable types of tobacco materials that may be used include, but are not limited to, flue-cured tobacco, Burley tobacco, Maryland tobacco, Oriental tobacco, rare tobacco, specialty tobacco, blends thereof and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass.

A formulation, which may include a pre-dispersion formulation or a pre-vapor formulation, is a material or combination of materials that may be transformed into a dispersion. For example, the formulation may be a liquid, solid and/or gel formulation including, but not limited to, water, beads, solvents, active ingredients, ethanol, plant materials including fibers and extracts, natural or artificial flavors, and/or dispersion formers such as glycerin and propylene glycol. The formulation may include those described in U.S. Patent Application Publication No. 2015/0020823 to Lipowicz et al. filed Jul. 16, 2014 and U.S. Patent Application Publication No. 2015/0313275 to Anderson et al. filed Jan. 21, 2015, the entire contents of each of which is incorporated herein by reference thereto.

The formulation may include nicotine or may exclude nicotine. The formulation may include one or more tobacco flavors. The formulation may include one or more flavors which are separate from the one or more tobacco flavors.

In some example embodiments, a formulation that includes nicotine may also include one or more acids. The one or more acids may be one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-penenoic acid, phenylacetic acid, 3-phenylpropionic acid, hydrochloric acid, phosphoric acid, sulfuric acid and combinations thereof.

In some example embodiments, a dispersion generator may generate a dispersion that is substantially free of one or more materials being in a gas phase. For example, the dispersion may include one or more materials substantially in a particulate phase and substantially not in a gas phase.

Figure 2A:
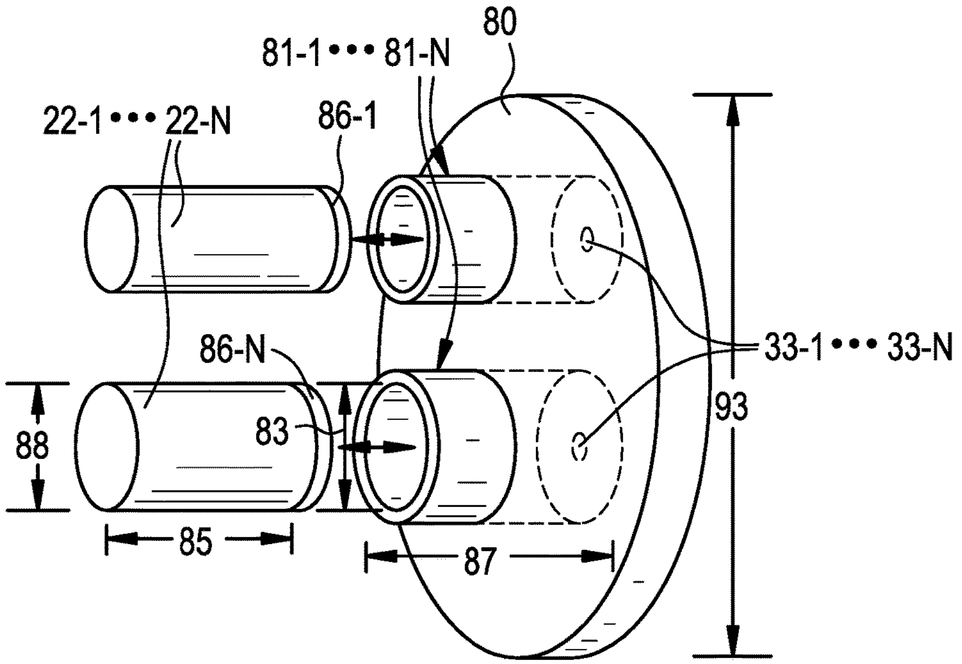
FIG. 2A is a perspective view of a cartridge holder according to some example embodiments.

FIG. 2A is a perspective view of a cartridge holder according to some example embodiments. The cartridge holder 80 shown in FIG. 2A may be the cartridge holder 80 included in FIG. 1A and FIG. 1B.

As shown in FIG. 2A, the cartridge holder 80 may include multiple separate slots 81-1 to 81-N. The cartridge holder 80 may have a diameter 93 corresponding to a diameter of at least one of an e-vaping device 60 and a base 71. Each of slots 81-1 to 81-N may extend a length 87. At least part of the length 87 of at least one of slots 81-1 to 81-N may extend into the cartridge holder 80. The length 87 of at least one of slots 81-1 to 81-N may be less than a full length 85 of at least one of cartridges 22-1 to 22-N that the given at least one of slots 81-1 to 81-N is configured to receive. As a result, at least one of cartridges 22-1 to 22-N inserted into a given slot of slots 81-1 to 81-N, such that the cartridge of cartridges 22-1 to 22-N completely fills the given slot of slots 81-1 to 81-N and/or may at least partially extend out of the slot of slots 81-1 to 81-N. Each of slots 81-1 to 81-N may have a given diameter 83. The diameter 83 of a given slot of slots 81-1 to 81-N may correspond to an external diameter 88 of at least one of cartridges 22-1 to 22-N that the given slot of slots 81-1 to 81-N is configured to receive. Different slots 81-1 to 81-N included in the cartridge holder 80 may be configured to receive different cartridges 22-1 to 22-N. Thus, different slots 81-1 to 81-N may have different dimensions, including different diameters 83, lengths 87, shapes, and some combination thereof.

In some example embodiments, a cartridge holder 80 may include at least one of connectors 33-1 to 33-N that at least partially extends into at least one of slots 81-1 to 81-N. A portion of a connector of connectors 33-1 to 33-N that extends into a slot of slots 81-1 to 81-N may be referred to herein as a portion of the connector of connectors 33-1 to 33-N that is included in the slot of slots 81-1 to 81-N.

The portion of a given connector of connectors 33-1 to 33-N included in a given slot of slots 81-1 to 81-N may include an electrical interface configured to electrically couple with at least one of connector of at least one of cartridges 22-1 to 22-N. For example, connector 33-1 included in slot 81-1 may be configured to electrically couple with a connector 86-1 of the given cartridge 22-1. The slot 81-1 may hold the cartridge 22-1 in contact with the connector 33-1.

The portion of a given connector of connectors 33-1 to 33-N included in a given slot of slots 81-1 to 81-N may include a connection interface configured to directly couple, connect, etc. with at least one connector of at least one of cartridges 22-1 to 22-N. For example, connector 33-1 included may be configured to connect with a connector 86-1 of the given cartridge 22-1 when the cartridge 22-1 is inserted into the slot 81-1. The connector 33-1 may be configured to electrically couple a cartridge 22-1 with a power supply via directly connecting with a connector 86-1 of the cartridge 22-1.

In some example embodiments, a given slot of slots 81-1 to 81-N is configured to accommodate one or more different cartridges 22-1 to 22-N. For example, a slot 81-1 may accommodate a first cartridge of cartridges 22-1 to 22-N that includes a vaporizer assembly, and the slot 81-1 may alternatively accommodate a second cartridge of cartridges 22-1 to 22-N that includes an atomizer assembly. The first and second cartridges 22-1 to 22-N may be interchangeably swapped from the slot 81-1. For example, the first and second cartridges 22-1 to 22-N may each have a connector 86-1 configured to connect with the connector 33-1 coupled to the given slot 81-1.

Because different cartridges 22-1 to 22-N may be interchangeably installed, removed, etc. from one or more of the slots 81-1 to 81-N, and because different cartridges 22-1 to 22-N may include different dispersion generators, the e-vaping device 60 may be configured to generate various combined dispersions as desired by an adult vaper. The adult vaper may install selected cartridges 22-1 to 22-N in one or more of the slots 81-1 to 81-N, swap a cartridge of cartridges 22-1 to 22-N in a slot of slots 81-1 to 81-N for a different cartridge of cartridges 22-1 to 22-N as desired, etc. As a result, the adult vaper may customize the combined dispersion provided by the e-vaping device, thereby customizing the sensory experience provided by the e-vaping device 60. Furthermore, the e-vaping device 60 enables the combined dispersion to be generated with mitigated risk of chemical reactions between the separate dispersions that combine to generate the combined dispersion.

Figure 2B:
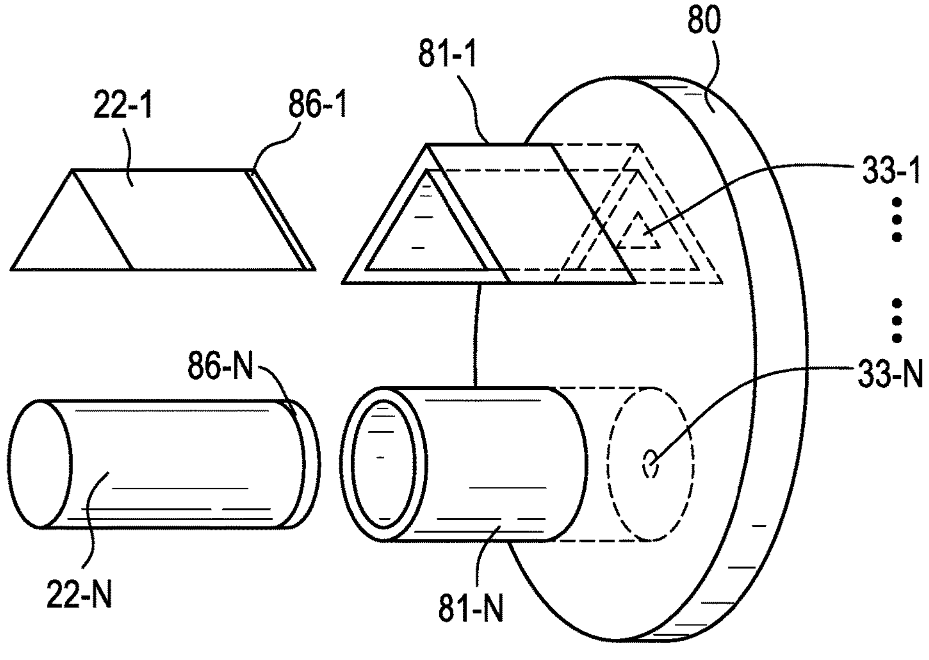
FIG. 2B is a perspective view of a cartridge holder according to some example embodiments.

FIG. 2B is a perspective view of a cartridge holder according to some example embodiments. The cartridge holder 80 shown in FIG. 2B may be the cartridge holder 80 included in FIG. 1A and FIG. 1B.

In some example embodiments, a cartridge holder 80 includes various connectors 33-1 to 33-N configured to couple with different sets of dispersion generators. The cartridge holder 80 may include various slots 81-1 to 81-N configured to receive different various cartridges 22-1 to 22-N. As a result, a given one of connectors 33-1 to 33-N, a given one of slots 81-1 to 81-N, or some combination thereof, may be restricted to being coupled with a first cartridge of cartridges 22-1 to 22-N and may be restricted from being coupled with a second cartridge of cartridges 22-1 to 22-N.

In some example embodiments, a cartridge holder 80 includes separate slots 81-1 to 81-N having different diameters and lengths, where separate slots have separate dimensions corresponding to different cartridges 22-1 to 22-N, such that the separate, respective slots 81-1 to 81-N are configured to receive different cartridges 22-1 to 22-N.

Because the cartridge holder 80 may include different connectors 33-1 to 33-N configured to couple with different sets of cartridges 22-1 to 22-N, the cartridge holder 80 may enable different types of dispersion generators (e.g., vaporizer assemblies, atomizer assemblies, etc.) included in different cartridges 22-1 to 22-N to be included in a common at least one of an e-vaping device 60 and a base 71. In addition, the cartridge holder may enable different cartridges including different dispersion generators, even dispersion generators of a common type, to be included in a common at least one of an e-vaping device 60 and a base 71 even through the different dispersion generators may have different connectors, dimensions, etc. As a result, the diversity and range of sensory experiences that may be provided by at least one of an e-vaping device and a base to which various dispersion generators are coupled via the cartridge holder 80, etc. may be improved.

As shown in FIG. 2B, the cartridge holder 80 includes connectors 33-1 to 33-N included in respective slots 81-1 to 81-N. Connector 33-1 is configured to couple with connector 86-1 of cartridge 22-1 and is restricted from coupling with connector 86-N of cartridge 22-N. For example, connectors 33-1 and 86-1 may be complementary bayonet connector elements, and connector 86-N may be a threaded connector, such that connector 33-1 is restricted from coupling with connector 86-N.

Connector 33-N is configured to couple with connector 86-N of cartridge 22-N and is restricted from coupling with connector 86-1 of cartridge 22-1. For example, connectors 33-N and 86-N may be complementary threaded connector elements, and connector 86-1 may be a bayonet connector, such that connector 33-N is restricted from coupling with connector 86-1.

As also shown, cartridge holder 80 includes slots 81-1 and 81-N, where the respective slots have different dimensions corresponding to respective dimensions of the different cartridges 22-1 and 22-N. As a result, slot 81-1 is configured to receive cartridge 22-1 and slot 81-N is configured to receive cartridge 22-N, and slot 81-1 is restricted from receiving cartridge 22-N and slot 81-N is restricted from receiving cartridge 22-1. Such restrictions may prevent incorrect couplings of various cartridges 22-1 to 22-N with connectors 33-1 to 33-N. In addition, such restrictions may restrict the various cartridges 22-1 to 22-N that may be coupled to the connectors 33-1 to 33-N to particular sets of cartridges 22-1 to 22-N having particular sets of dimensions. As a result, the sensory experience provided may be improved, as at least one of an e-vaping device 60 and a base 71 that includes the cartridge holder 80 may be restricted from coupling with certain sets of cartridges 22-1 to 22-N, thereby restricting at least one of an e-vaping device 60 and a base 71 from providing a certain set of dispersions.

Figure 2C:
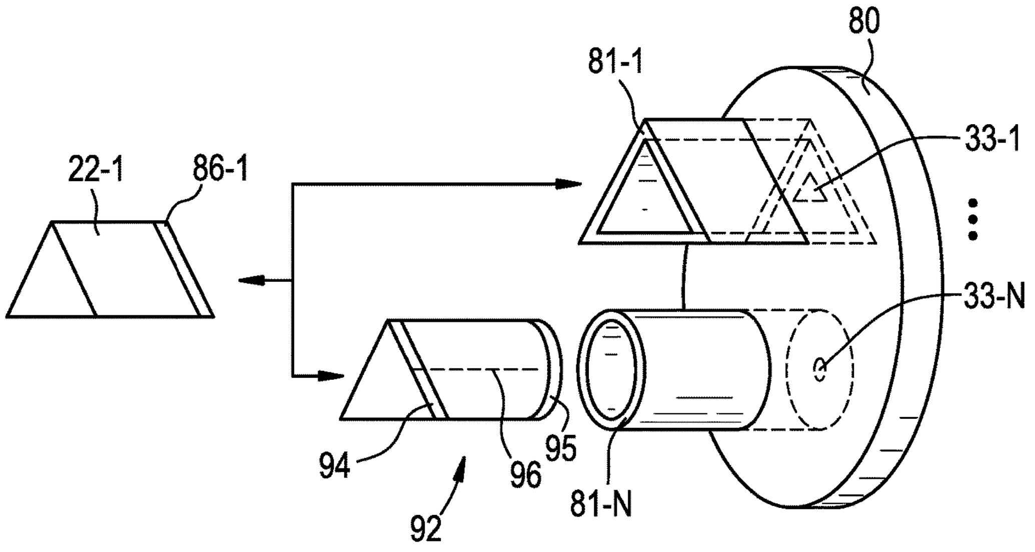
FIG. 2C is a perspective view of a cartridge holder according to some example embodiments.

FIG. 2C is a perspective view of a cartridge holder according to some example embodiments. The cartridge holder 80 shown in FIG. 2C may be the cartridge holder 80 included in FIG. 1A and FIG. 1B.

In some example embodiments, a cartridge holder 80 may couple with a cartridge 22-1 via a connector 33-N that is restricted from being directly coupled with a connector 86-1 of the cartridge 22-1. An adapter 92 may enable such coupling. The adapter 92 may include a first connector 95 configured to directly couple with a connector 33-N of the cartridge holder 80 and a second connector 94 configured to directly couple with a connector 86-1 of the cartridge 22-1. The connectors 94, 95 may be electrically coupled 96, so that directly coupling connectors 86-1 and 94, along with coupling connectors 95 and 33-N, electrically couples the cartridge 22-1 to at least the connector 33-N.

As shown, at least one connector 33-1 of the cartridge holder 80 may be configured to couple with a connector 86-1 of the cartridge 22-1, and the adapter 92 may be configured to enable connector 33-N to couple with the cartridge 22-1 even through the connector 33-N may be restricted from directly coupling to connector 86-1. In some example embodiments, none of the connectors 33-1 to 33-N of the cartridge holder 80 may be configured to couple with a connector 86-1 of the cartridge 22-1, and the adapter 92 may be configured to enable at least one connector 33-1 to 33-N to couple with the cartridge 22-1. Thus, at least one of an e-vaping device 60 and a base 71 in which the cartridge holder 80 is included may provide dispersions generated by a dispersion generator included in the cartridge 22-1 during vaping.

As a result, the adapter and the cartridge holder 80 may enable a dispersion generator to be coupled to the connector, where the dispersion generator would otherwise be restricted from being coupled to a connector of the cartridge holder. As a result, a diversity of sensory experiences that may be provided via one or more adult vapers is improved.

Figure 3A:
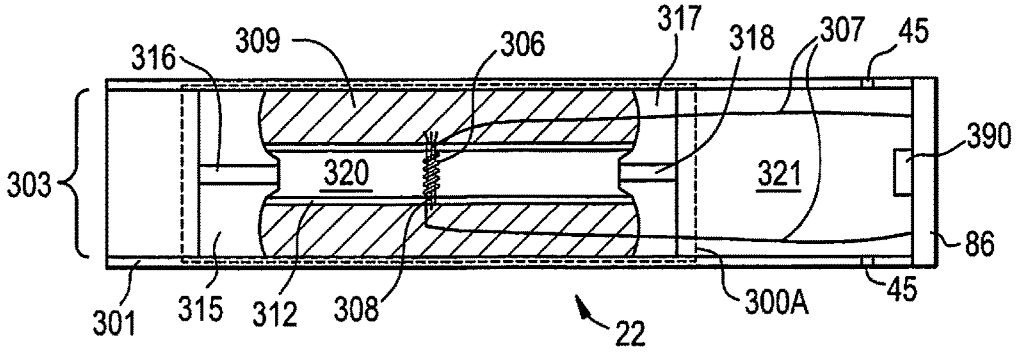
FIG. 3A is a cartridge that includes a dispersion generator according to some example embodiments.

FIG. 3A is a cartridge 22 that includes a dispersion generator 300A according to some example embodiments. FIG. 3B is a cartridge 22 that includes a dispersion generator 300B according to some example embodiments. FIG. 3C is a cartridge 22 that includes a dispersion generator 300C according to some example embodiments. Each of the cartridges 22 shown in FIG. 3A, FIG. 3B, and FIG. 3C may be included in any and all embodiments of cartridges included herein, including one or more of the cartridges 22-1 to 22-N shown in FIG. 1B.

In some example embodiments, one or more different cartridges may be included in an e-vaping device. The different cartridges may include different dispersion generators. Different dispersion generators may generate separate dispersions independently, and the separate dispersions may subsequently combine to generate a combined dispersion.

In some example embodiments, dispersion generators may be vaporizer assemblies, atomizer assemblies, or some combination thereof. A vaporizer assembly generates a dispersion that is a vapor. A vaporizer assembly is configured to generate a vapor based on heating a pre-vapor formulation to vaporize the pre-vapor formulation. An atomizer assembly is configured to generate an aerosol based on applying a mechanical force to a pre-dispersion formulation that is a pre-aerosol formulation.

FIG. 3A illustrates a cartridge 22 that includes a dispersion generator 300A that is a vaporizer assembly, according to some example embodiments. As shown in FIG. 3A, the dispersion generator 300A may include a reservoir 309 for a pre-vapor formulation, a wick 308 that is configured to draw the pre-vapor formulation from the reservoir 309, and a heater 306 that may heat the drawn pre-vapor formulation to vaporize the pre-vapor formulation and generate a vapor.

The cartridge 22 may include an outer housing 301 extending in a longitudinal direction and an inner tube 312 coaxially positioned within the outer housing 301. The outer housing 301 may have a generally cylindrical cross-section. In some example embodiments, the outer housing 301 may have a generally triangular cross-section. In some example embodiments, the housing 301 may have a greater circumference or dimensions at a tip end than at an outlet end of the cartridge 22.

The cartridge 22 may include a connector 86 at a tip end. The connector 86 may be configured to physically couple with an interface included in one or more sections of at least one of an e-vaping device 60 and a base 71.

In some example embodiments, the connector 86 includes an electrical interface. The electrical interface may be configured to electrically couple one or more portions of the cartridge 22 to a power supply based on the connector 86 coupling with a portion of one or more sections of at least one of an e-vaping device 60 and a base 71, including a power supply section 72 of the at least one of an e-vaping device 60 and a base 71. In the illustrated embodiment, for example, heater 306 is electrically coupled to connector 86 via electrical leads 307. The heater 306 may be supplied with electrical power from a power supply to which the connector 86 and leads 307 electrically couple the heater 306.

At one end of the inner tube 312, a nose portion of a gasket (or seal) 317 may be fitted into an end portion of the inner tube 312, while an outer perimeter of the gasket 317 may provide a substantially tight seal with an interior surface of the outer housing 301. The gasket 317 may also include a central, longitudinal channel 318, which opens into an interior of the inner tube 312 that defines a central channel 320. A space 321 at a backside portion of the gasket 317 may intersect and communicate with the central channel 318 of the gasket 317. This space 321 assures communication between the central channel 318 and one or more air inlet ports 45.

In some example embodiments, a nose portion of another gasket 315 may be fitted into another end portion of the inner tube 312. An outer perimeter of the gasket 315 may provide a substantially tight seal with an interior surface of the outer housing 301. The gasket 315 may include a central channel 316 disposed between the central channel 320 of the inner tube 312 and an opening 303 at an outlet end of the housing 301. The central channel 316 may transport a vapor from the central channel 320 to the opening 303 to exit the dispersion generator 300A.

The space defined between the gaskets 315 and 317 and the outer housing 301 and the inner tube 312 may establish the confines of the reservoir 309. The reservoir 309 may include a pre-vapor formulation, and optionally a storage medium configured to store the pre-vapor formulation therein. The storage medium may include a winding of cotton gauze or other fibrous material about a portion of the dispersion generator 300A. The reservoir 309 may be contained in an outer annulus between the inner tube 312 and the outer housing 301 and between the gaskets 315 and 317. Thus, the reservoir 309 may at least partially surround the central channel 320. The heater 306 may extend transversely across the central channel 320 between opposing portions of the reservoir 309. In some example embodiments, the heater 306 may extend parallel to a longitudinal axis of the central channel 320.

The storage medium of the reservoir 309 may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section which has a Y-shape, cross shape, clover shape or any other suitable shape. In an alternative example embodiment, the reservoir 309 may include a filled tank lacking any storage medium and containing only pre-vapor formulation.

The reservoir 309 may be sized and configured to hold enough pre-vapor formulation such that the dispersion generator 300A may be configured for vaping for at least about 200 seconds. The dispersion generator 300A may be configured to allow each vaping to last a maximum of about 5 seconds.

The dispersion generator 300A may include a wick 308 configured to draw pre-vapor formulation from the reservoir 309, such that the pre-vapor formulation may be vaporized from the wick based on heating of the wick 308 by the heater 306. During vaping, pre-vapor formulation may be transferred from the reservoir 309 and/or storage medium in the proximity of the heater 306 via capillary action of a wick 308. The wick 308 may include a first end portion and a second end portion, which may extend into opposite sides of the reservoir 309. Wick end portions may be referred to herein as wick roots. The heater 306 may at least partially surround a central portion of the wick such that when the heater 306 is activated, the pre-vapor formulation in the central portion of the wick 308 may be vaporized by the heater 306 to generate a vapor. The central portion of a wick may be referred to herein as a wick trunk.

The wick 308 may include filaments (or threads) having a capacity to draw the pre-vapor formulation. For example, a wick may be a bundle of glass (or ceramic) filaments, a bundle including a group of windings of glass filaments, etc., all of which arrangements may be capable of drawing pre-vapor formulation via capillary action by interstitial spacings between the filaments. The filaments may be generally aligned in a direction perpendicular (transverse) to the longitudinal direction of the dispersion generator 300A. In an example embodiment, the wick may include one to eight filament strands, each strand comprising a plurality of glass filaments twisted together. The end portions of the wick may be flexible and foldable into the confines of the reservoir 309. The filaments may have a cross-section that is generally cross-shaped, clover-shaped, Y-shaped, or in any other suitable shape.

The wick 308 may include any suitable material or combination of materials. Examples of suitable materials may be, but not limited to, glass, ceramic- or graphite-based materials. The wick may have any suitable capillarity drawing action to accommodate pre-vapor formulations having different physical properties such as density, viscosity, surface tension and vapor pressure.

In some example embodiments, the heater 306 may include a wire coil which at least partially surrounds the wick 308 in the dispersion generator 300A. The wire may be a metal wire and/or the wire coil may extend fully or partially along the length of the wick. The wire coil may further extend fully or partially around the circumference of the wick. In some example embodiments, the wire coil may or may not be in contact with the wick.

The wire coil may be formed of any suitable electrically resistive materials. Examples of suitable electrically resistive materials may include, but not limited to, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heater 306 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heater 306 may include at least one material selected from the group consisting of stainless steel, copper, copper alloys, nickel-chromium alloys, super alloys and combinations thereof. In an example embodiment, the heater 306 may be formed of nickel-chromium alloys or iron-chromium alloys. In another example embodiment, the heater 306 may be a ceramic heater having an electrically resistive layer on an outside surface thereof.

The heater 306 may heat pre-vapor formulation in the wick 308 by thermal conduction. Alternatively, heat from the heater 306 may be conducted to the pre-vapor formulation by means of a heat conductive element or the heater 306 may transfer heat to the incoming ambient air that is drawn through the dispersion generator 300A during vaping, which in turn heats the pre-vapor formulation by convection.

It should be appreciated that, instead of using a wick, the heater 306 may be a porous material which incorporates a resistance heater formed of a material having a high electrical resistance capable of generating heat quickly.

The cartridge 22 may include an opening 303 in the housing 301. A vapor generated by the heater 306 of the dispersion generator 300A may be directed out of the dispersion generator 300A through the central channel 316 and the opening 303 to exit the cartridge 22.

In some example embodiments, a cartridge 22 includes one or more storage devices 390. A storage device 390 may be configured to be electrically, communicatively coupled to connector 86. The storage device 390 may include information associated with the dispersion generator 300 included in the cartridge 22 in which the storage device 390 is included. Such information may be referred to as "cartridge information," where the cartridge information stored in a storage device 390 of a given cartridge 22 includes information associated with the dispersion generator included in the given cartridge. The cartridge information associated with the dispersion generator 300 may include information uniquely identifying one or more elements of the dispersion generator, including the dispersion generator 300 itself, a formulation held by the dispersion generator 300, information indicating a dispersion generator "type" of the given dispersion generator 300 (e.g., vaporizer assembly or atomizer assembly), or some combination thereof. Formulation information may include information indicating a flavor associated with a dispersion generated by the given dispersion generator 300, viscosity information associated with the formulation, etc. The information may indicate one or more parameters of electrical power to be supplied to the dispersion generator 300 via connector 86 during vaping, including one or more of a particular voltage, current, time period during which to supply the electrical power, etc. The information may indicate a particular sequence according to which the dispersion generator is to be activated.

The cartridge information associated with the dispersion generator 300, stored in the storage device 390, may be accessed via connector 86 by control circuitry 11 included in at least one of an e-vaping device 60 and a base 71 to which the given dispersion generator 300 may be coupled through connector 86. The control circuitry 11 may independently control dispersion generation by one or more dispersion generators 300 based on the accessed cartridge information.

In some example embodiments, a dispersion generator is configured to generate a vapor independently of a heater being included in the dispersion generator. For example, a dispersion generator may be an atomizer assembly that includes at least one of a fluid sprayer or a compressed gas emitter.

Figure 3B:
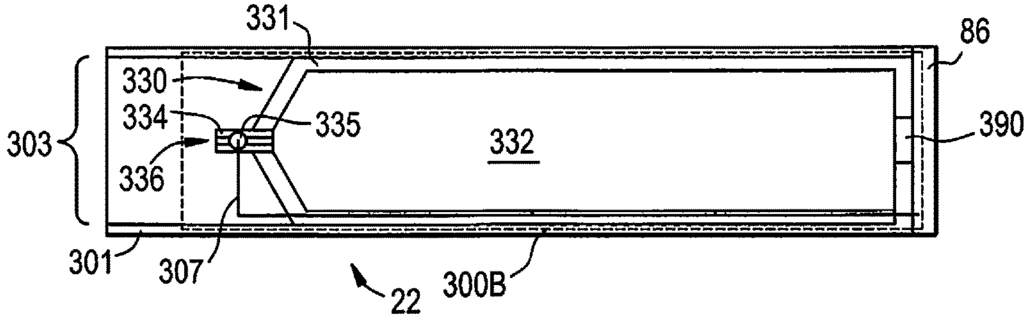
FIG. 3B is a cartridge that includes a dispersion generator according to some example embodiments.

As shown in FIG. 3B, a dispersion generator 300B included in a cartridge 22 may be an atomizer assembly that includes a pre-aerosol formulation emitter 330 configured to release a pre-aerosol formulation into an external environment to generate an aerosol. The emitter 330 may be one or more of a fluid sprayer, compressed gas emitter, etc. As shown, the emitter 330 includes a reservoir housing 331 in which a pre-aerosol formulation 332 is held. In some example embodiments, the reservoir housing 331 is at least partially incorporated into the outer housing 301 of the cartridge 22.

In some example embodiments, the emitter 330 holds a pre-aerosol formulation at an elevated pressure, relative to an external environment of the emitter 330. For example, the pre-aerosol formulation may be a pressurized gas.

The emitter 330 includes a dispensing interface 334 configured to release the pre-aerosol formulation 332 into the external environment through opening 303. The dispensing interface 334 may be electrically coupled to connector 86 via one or more electrical leads 307, such that one or more portions of the interface 334 may be selectively controlled to release a pre-aerosol formulation.

The dispensing interface includes a channel 336 and a dispensing control element 335. The element 335 controls a release of the pre-aerosol formulation into the external environment via channel 336. In some example embodiments, the element 335 is a valve assembly. A valve assembly may be controlled to release pre-aerosol formulation based on a supply of electrical power to the valve assembly via leads 307.

For example, where the emitter 330 is a pressurized gas emitter, the element 335 may be a valve assembly configured to selectively release pressurized gas 332 to generate an aerosol. In some example embodiments, the pre-aerosol formulation 332 is held in the housing 331 in a phase that is separate from a pure gas phase and at an elevated pressure, and the emitter 330 is configured to generate an aerosol based on a pressure differential across an element 335 that includes a valve assembly as the pre-aerosol formulation passes through the channel 336 to the external environment.

In another example, where the emitter 330 is a fluid sprayer, the element 335 may be a sprayer assembly configured to spray a fluid pre-aerosol formulation 332 into the external environment to generate an aerosol. In some example embodiments, the sprayer assembly includes a pump device.

In some example embodiments, the pre-aerosol formulation 332 includes a volatile substance, and the volatile substance may vaporize to generate an aerosol when the pre-aerosol formulation 332 is released into an external environment by the dispensing interface 334.

In some example embodiments, a dispersion generator is configured to generate a dispersion independently of a supply of electrical power. The dispersion generator, in some example embodiments, is a vaporizer assembly configured to generate a vapor based on evaporation of a volatile pre-vapor formulation. As shown in FIG. 3C, the dispersion generator 300C included in a cartridge 22 is a vaporizer assembly that includes a reservoir 309 and a wick 308 configured to draw pre-vapor formulation from the reservoir 309 into central channel 320. The pre-vapor formulation held by the reservoir may include a volatile substance.

Figure 3C:
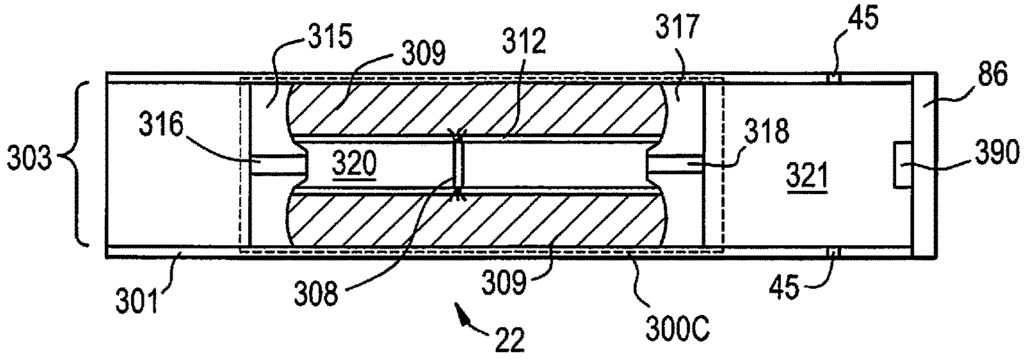
FIG. 3C is a cartridge that includes a dispersion generator according to some example embodiments.

As shown in FIG. 3C, a heater may be absent from the dispersion generator 300C. As also shown, electrical leads coupled to connector 86 are absent from the dispersion generator 300C. In some example embodiments, connector 86 is configured to physically couple with a portion of an e-vaping device and is isolated from electrically coupling at least some portions of the dispersion generator 300C to one or more portions of the e-vaping device. In some example embodiments, the connector 86 is configured to electrically couple a storage device 390 with a portion of at least one of an e-vaping device 60 and a base 71, such that cartridge information stored on the storage device 390 may be accessed by control circuitry 11 included in the at least one of an e-vaping device 60 and a base 71.

The dispersion generator 300C may be referred to as a "passive" vaporizer assembly, as it does not utilize electrical power to generate a vapor. As shown, the cartridge 22 in which the dispersion generator 300C is included further includes inlet ports 45. The inlet ports 45 are in flow communication with space 321. Air drawn into space 321 via inlet ports 45 may be drawn through central channels 318, 320, and 316 towards opening 303. Air passing through central channel 320 may draw vaporized pre-vapor formulation into the airstream to generate a vapor. The pre-vapor formulation may vaporize in the channel based on evaporation from the wick 308. Such vaporization may be based on a vapor pressure of the pre-vapor formulation and a pressure differential caused by the flow of air through the channel 320. In some example embodiments, pre-vapor formulations are eluted into an airstream from wick 308 to generate a vapor.

In some example embodiments, a dispersion generator is a vaporizer assembly configured to generate a vapor using heat generated in a separate dispersion generator. For example, where cartridges 22 that respectively include a separate one of dispersion generators 300A and 300C are positioned adjacently in at least one of an e-vaping device 60 and a base 71, heat generated by a heater 306 of the dispersion generator 300A may also heat one or more of the reservoir 309 or wick 308 of dispersion generator 300C. The heated reservoir 309 or wick 308 may cause pre-vapor formulation to be vaporized in the channel 320 to generate a vapor.

In some example embodiments, an e-vaping device includes control circuitry 11 configured to activate a first dispersion generator to cause a second dispersion generator to generate a vapor based on heat generated at the first dispersion generator. The control circuitry 11 may independently control the first dispersion generator to cause the second dispersion generator to generate the vapor based on cartridge information associated with the second dispersion generator, where the cartridge information is accessed from a storage device included in the second dispersion generator.

Figure 4:
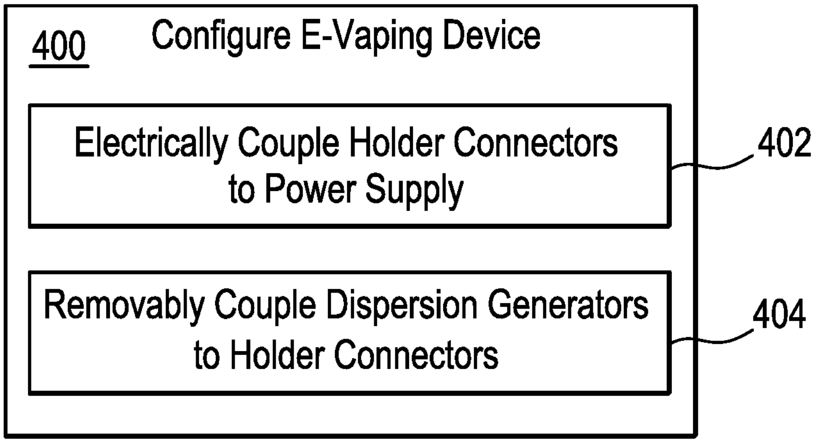
FIG. 4 is a flowchart illustrating a method of configuring an e-vaping device according to some example embodiments.

FIG. 4 is a flowchart illustrating a method of configuring 400 at least one of an e-vaping device and a base according to some example embodiments. The configuring 400 may be implemented with regard to any and all embodiments of e-vaping devices, bases, etc. included herein. In some example embodiments, one or more portions of the configuring are implemented by a configuror. The configuror may be one or more of a human operator, a machine, some combination thereof, etc. The machine may be a fabrication machine. The machine may be a special purpose machine configured to implement the configuring 400 based on executing program code stored in a memory device.

Referring to FIG. 4, at 402, the configuror electrically couples one or more connectors included in a cartridge holder to a power supply of the at least one of an e-vaping device and a base. The electrically coupling may include connecting the cartridge holder to a power supply section that includes the power supply, such that one or more connectors included in the cartridge holder are electrically coupled to the power supply section via one or more electrical leads, connectors, circuits, cathode connectors, anode, connectors, some combination thereof, etc.

At 404, the configuror removably couples one or more dispersion generators to one or more of the connectors of the cartridge holder. The removably coupling may include directly connecting a connector of the cartridge holder with a connector of a cartridge in which a dispersion generator is included. The removably coupling may include directly coupling a connector of the cartridge holder with a first connector of an adapter and directly coupling a second connector of the adapter with a connector of a cartridge in which a dispersion generator is included, where the first and second connectors of the adapter are electrically coupled. The removably coupling may include electrically coupling one or more of the dispersion generators to at least the power supply included in the power supply section via one or more of the connectors of the cartridge holder. The one or more dispersion generators may be multiple, different dispersion generators. For example, at least one of the dispersion generators may be a vaporizer assembly, and at least one of the dispersion generators may be an atomizer assembly. Separate dispersion generators of the multiple, different dispersion generators may be included in separate cartridges.

Removably coupling a cartridge in which a dispersion generator is included may include removably coupling the dispersion generator, and removably coupling a dispersion generator may be included in removably coupling a cartridge. Removably coupling a cartridge that includes a dispersion generator with a connector of the cartridge holder may include communicatively coupling at least a storage device of the cartridge with control circuitry included in the at least one of an e-vaping device and a base. The control circuitry may independently control dispersion generation by one or more of the removably coupled dispersion generators based on cartridge information accessed from one or more storage devices of one or more of the removably coupled dispersion generators. The cartridge holder may include one or more connectors in a slot, and removably coupling a dispersion generator with the one or more connectors may include removably inserting the dispersion generator into a slot to couple a connector of the dispersion generator with the connector of the cartridge holder. One or more portions of the slot, including one or more internal sidewalls of the slot, may structurally support the dispersion generator in contact with a connector of the cartridge holder. The one or more removably coupled dispersion generators may be removed, swapped, interchanged, etc.

Figure 5:
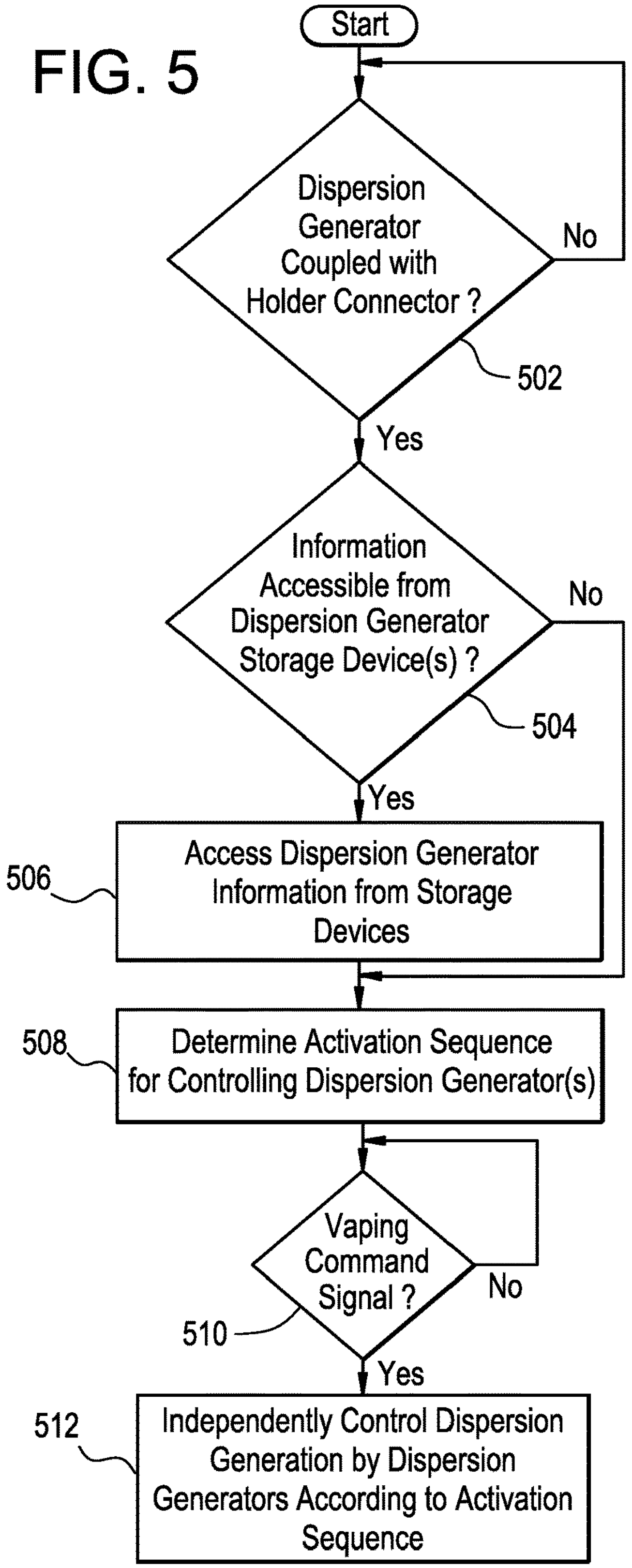
FIG. 5 is a flowchart illustrating a method of independently controlling electrical power supplied to one or more dispersion generators according to some example embodiments.

FIG. 5 is a flowchart illustrating a method of independently controlling electrical power supplied to one or more dispersion generators according to some example embodiments. The independently controlling shown in FIG. 5 may be implemented by control circuitry included in one or more e-vaping devices, bases, etc. according to any of the embodiments included herein.

Referring to FIG. 5, at 502, the control circuitry determines whether one or more dispersion generators are coupled with one or more connectors included in the at least one of an e-vaping device and a base, such that the control circuitry is communicatively coupled with at least a portion of each of the one or more dispersion generators. The portion may include a storage device included in a dispersion generator, and the communicatively coupling of the control circuitry and the storage device may enable data communication between the control circuitry and the storage device.

At 504, the control circuitry determines whether the control circuitry is communicatively coupled with a storage device of a dispersion generator, where the storage device includes cartridge information associated with the respective dispersion generator of the cartridge in which the storage device is included, and where the cartridge information is accessible by the control circuitry. If so, at 506, the control circuitry accesses the cartridge information from the storage device. The accessing of the cartridge information may include downloading at least a portion of the cartridge information to the control circuitry, processing at least a portion of the cartridge information, some combination thereof, etc.

At 508, the control circuitry determines an activation sequence according to which the control circuitry will independently control one or more dispersion generators coupled to the at least one of an e-vaping device and a base in which the control circuitry is coupled. Where cartridge information associated with one or more dispersion generators is accessed at 506, the determining at 508 may include determining an activation sequence based on one or more portions of the accessed cartridge information. In some example embodiments, the control circuitry determines an activation sequence that includes independently controlling a dispersion generator, where the activation sequence is determined based on cartridge information associated with another, separate dispersion generator included in another, separate cartridge.

At 510 and 512, the control circuitry independently controls dispersion generation by one or more of the coupled dispersion generators according to the determined activation sequence, in response to determining that a vaping command signal is received at the control circuitry. The vaping command signal may be generated by one or more of an interface, a sensor, etc.

In some example embodiments, at least one of an e-vaping device and a base is configured to provide a vapor having at least two distinct particle size distributions. A first particle size distribution may be generated using a vaporizer assembly that generates a vapor by heating a pre-vapor formulation. A second particle size distribution may be generated using an atomizer assembly that generates an aerosol by mechanical action on a pre-aerosol formulation. The vapor and aerosol may combine to generate a gaseous dispersion that is provided via an outlet of the e-vaping device during vaping. The gaseous dispersion may be included in a combined dispersion.

By providing a gaseous dispersion with at least two different particle size distributions, the gaseous dispersion may be tailored to provide desired flavor and/or therapeutic compositions. For example, flavor compounds may have a larger median particle size so as to be deposited in a first location. In addition, functional compounds, such as nicotine and/or therapeutic compounds may be provided in smaller particle sizes so as to deliver the particles to a second location.

Figure 6:
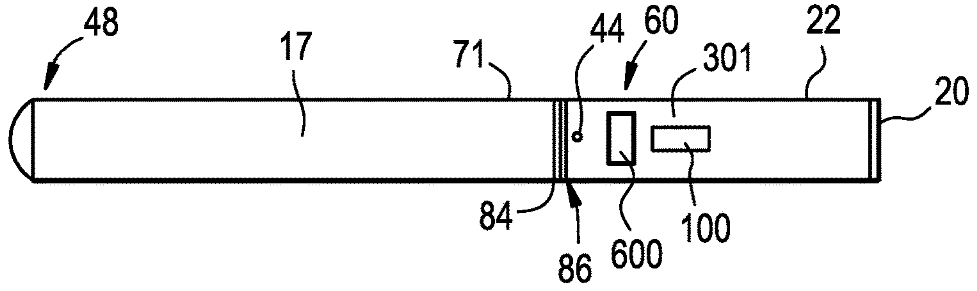
FIG. 6 is a side view of an e-vaping device according to some example embodiments.

FIG. 6 is a side view of an e-vaping device 60 according to some example embodiments. The cartridge 22 shown in FIG. 6 may be included in any and all embodiments of cartridges included herein, including any one of the cartridges 22 included in at least FIG. 3A, FIG. 3B, and FIG. 3C, FIG. 7, FIG. 8, FIG. 9, and FIG. 10.

In some example embodiments, a cartridge 22 may be coupled to a base 71, such that an e-vaping device 60 includes a cartridge 22 and a base 71 coupled together. The cartridge holder 80 may be absent from the base 71. As shown in FIG. 6, an e-vaping device 60 may include a cartridge 22 coupled to a reusable base (or second section) 71, where a cartridge holder 80 is absent from base 71. As shown, the cartridge 22 may be coupled, via the connector 86 of the cartridge 22, to an interface 84 of the base 71. A window 100 may be formed in the outer housing 301 of the cartridge 22 to allow viewing of the tanks so as to enable viewing of the pre-vapor formulation included in the cartridge 22 and determination of an amount of pre-vapor formulation remaining in the cartridge 22. A button 600 may be included on the outer surface of the housing 301 to enable manual activation of the e-vaping device 60 via manual interaction with the button 600. The e-vaping device 60 may include an outlet end insert 20.

In some example embodiments, the cartridge 22 is disposable and the base 71 is reusable. In some example embodiments, the cartridge 22 and the base 71 are disposable.

Figure 7:
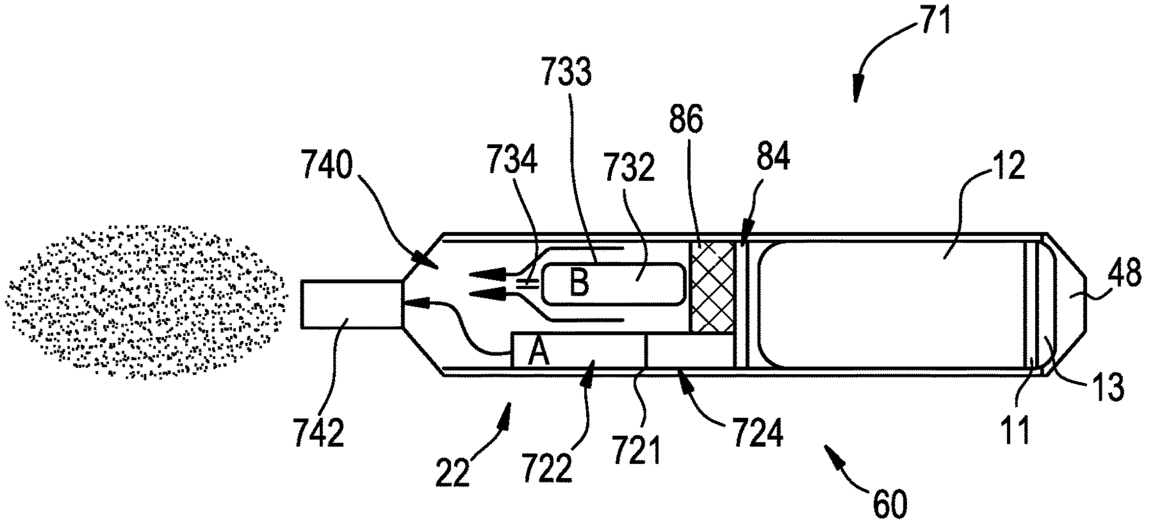
FIG. 7 is a schematic view of an e-vaping device according to some example embodiments.

FIG. 7 is a schematic view of an e-vaping device 60 according to some example embodiments. The cartridge 22 shown in FIG. 7 may be included in any and all embodiments of cartridges included herein.

As shown in FIG. 7, in some example embodiments, the cartridge 22 may include multiple dispersion generators. As shown, the multiple dispersion generators in the e-vaping device 60 may include a vaporizer assembly 733 and an atomizer assembly 721. The vaporizer assembly 733 may be configured to generate a vapor based on heating a pre-vapor formulation to a temperature sufficient to vaporize the pre-vapor formulation. In some example embodiments, the atomizer assembly 721 includes a tank 723 and an atomizer 724. The atomizer 724 may include a pressurization arrangement and/or a piezoelectric element. The atomizer assembly 721 may be configured to generate a dispersion based on applying a mechanical force to a pre-dispersion formulation to generate a dispersion. In some example embodiments, applying a mechanical force to a pre-dispersion formulation includes mechanically shearing the pre-dispersion formulation. In some example embodiments, the e-vaping device 60 may include an outlet element 742 including a single outlet instead of the e-vaping device 60 including an outlet end insert 20 (as shown in FIG. 7).

Figure 8:
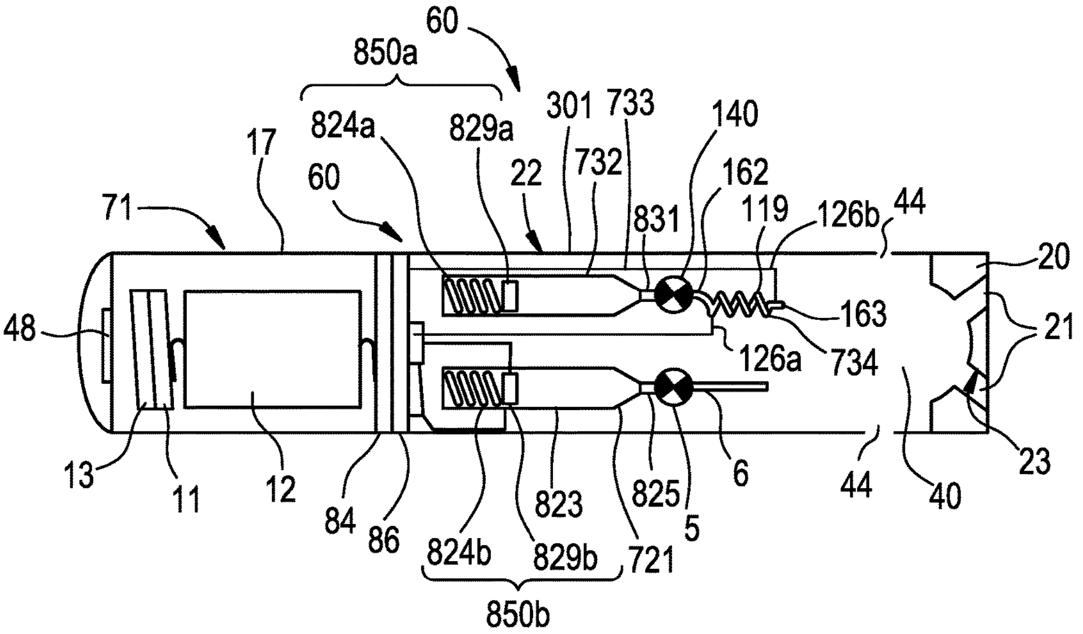
FIG. 8 is a cross-sectional view of the e-vaping device of FIG. 6 according to some example embodiments.

FIG. 8 is a cross-sectional view of the e-vaping device 60 of FIG. 6 according to some example embodiments. The cartridge 22 shown in FIG. 8 may be included in any and all embodiments of cartridges included herein.

In some example embodiments, as shown in FIG. 8, the vaporizer assembly 733 may include a vaporizer in the form of a capillary tube 734 and a tank 732. The capillary tube 734 may include a heatable portion 119 extending between two electrical leads 126*a*, 126*b*. The heatable portion 119 of the capillary tube 734 may be configured to heat the pre-vapor formulation in the heatable portion 119 of the capillary tube 734 to a temperature sufficient to vaporize the pre-vapor formulation.

In some example embodiments, the capillary tube 734 includes an inlet 162 in fluid communication with an outlet 831 of the tank 732. A valve 140 may be between the outlet 831 and the inlet 162 to reduce and/or substantially prevent release of the pre-vapor formulation when the e-vaping device is not activated. The valve 140 may be a solenoid valve. The capillary tube 734 also includes an outlet 163 configured to expel vapor from the capillary tube 734.

In some example embodiments, the valve 140 aids in limiting the amount of pre-vapor formulation that is drawn back from the capillary tube 734 upon release of pressure upon the tank 732. Withdrawal of pre-vapor formulation from the capillary tube 734 at conclusion of a vaping (or activation) is desirous. The presence of residual pre-vapor formulation in the capillary tube 734 at the initiation of a new vaping cycle may lead to undesirable sputtering of the pre-vapor formulation from the heated capillary tube 734 at the beginning of activation. The valve 140 may be configured to allow a desired, limited amount of drawback to occur, such that drawback of pre-vapor formulation occurs without air being drawn into the tank 732.

In some example embodiments, the tank 732 may be a tubular, elongate body that is configured to hold a quantity of the pre-vapor formulation. The tank 732 may be pressurized such that the pre-vapor formulation is under constant pressure. The tank 732 may include a pressurization arrangement 850*a* including a spring 824*a* and a piston 829*a*. The tank 732 may be compressible and may be formed of a flexible and/or elastic material. The tank 732 may extend longitudinally within the housing 301 of the cartridge 22.

In some example embodiments, the valve 140 is configured to reduce and/or substantially prevent flow of the pre-vapor formulation from the tank 732 when the e-vaping device 60 is not activated. When the valve 140 is opened, the tank 732 may release a volume of the pre-vapor formulation to the capillary tube 734 where the pre-vapor formulation is vaporized.

In some example embodiments, the capillary tube 734 is purged once air stops being drawn through the outlet ports 21 or manual interaction with the button 600 (shown in FIG. 6) ceases because any formulation remaining in the capillary tube 734 is vaporized during heating.

In some example embodiments, the capillary tube 734 has an internal diameter ranging from about 0.01 mm to about 10 mm, about 0.05 mm to about 1 mm, or about 0.05 mm to about 0.4 mm. A capillary tube 734 having a smaller diameter may provide more efficient heat transfer to the pre-vapor formulation because, with the shorter the distance to the center of the pre-vapor formulation, less energy and time is required to vaporize the pre-vapor formulation.

In some example embodiments, the capillary tube 734 may have a length ranging from about 5 mm to about 72 mm, about 10 mm to about 60 mm, or about 20 mm to about 50 mm. In some example embodiments, the capillary tube 734 may be about 50 mm in length and may include an about 40 mm long portion that forms a coiled heated section.

In some example embodiments, the capillary tube 734 is substantially straight. In other example embodiments, the capillary tube 734 may be coiled and/or include one or more bends therein to conserve space.

In some example embodiments, the capillary tube 734 is formed of a conductive material, and includes the heatable portion 119 through which current passes. The capillary tube 734 may be formed of any electrically conductive material that may be resistively heated, while retaining the necessary structural integrity at the operating temperatures experienced by the capillary tube 734, and which is non-reactive with the pre-vapor formulation. Suitable materials for forming the capillary tube 734 include stainless steel, copper, copper alloys, porous ceramic materials coated with film resistive material, Inconel® available from Special Metals Corporation, which is a nickel-chromium alloy, nichrome, which is also a nickel-chromium alloy, and combinations thereof.

In some example embodiments, the capillary tube 734 is a stainless steel capillary tube 734, a portion of which serves as the heatable portion 119. The heatable portion 119 is established between the electrical leads 126*a*, 126*b*. Thus, a direct or alternating current passes along a length of heatable portion 119 of the capillary tube 734 to form the heater. The stainless steel capillary tube 734 may be heated by resistance heating. The stainless steel capillary tube 734 may be circular in cross section. The capillary tube 734 may be of tubing suitable for use as a hypodermic needle of various gauges. For example, the capillary tube 734 may comprise a 32 gauge needle having an internal diameter of about 0.11 mm or a 26 gauge needle having an internal diameter of 0.26 mm.

In some example embodiments, the capillary tube 734 may be a non-metallic tube such as, for example, a glass tube. In such an embodiment, the heater is formed of a conductive material capable of being resistively heated, such as, for example, stainless steel, nickel-chromium, or platinum wire, arranged along the glass tube. When the heater is heated, the pre-vapor formulation in the capillary tube 734 may be heated to a temperature sufficient to at least partially vaporize the pre-vapor formulation in the capillary tube 734.

In some example embodiments, the electrical leads 126*a*, 126*b* may be bonded to the capillary tube 734. In some example embodiments, the electrical leads 126*a*, 126*b* are brazed to the capillary tube 734.

Once the capillary tube 734 is heated, the pre-vapor formulation contained within the heatable portion 119 of the capillary tube 34 may be vaporized and ejected out of the outlet 163. Upon being ejected out of the outlet 163, the pre-vapor formulation may expand and mix with air from one or more air inlet ports 44 in a mixing chamber 40.

In some example embodiments, when activated, the heatable portion 119 heats a portion of the pre-vapor formulation for less than about 10 seconds, or less than about 7 seconds. Thus, the power cycle (or maximum vaping length) may range in period from about 2 seconds to about 10 seconds (e.g., about 3 seconds to about 9 seconds, about 4 seconds to about 8 seconds or about 5 seconds to about 7 seconds).

In some example embodiments, as shown in FIG. 8, the atomizer assembly 721 may include a pressurization arrangement 850*b*. The pressurization arrangement 850*b* may include a spring 824*b* and a piston 829*b*. The pressurization arrangement 850*b* is configured to apply constant pressure to the pre-aerosol formulation in the tank 823. The tank 823 may be compressible and formed of a flexible and/or elastic material, such that the pre-aerosol formulation in the tank 823 is under constant pressure. A valve 5, which may be a solenoid valve, is configured to maintain the pre-aerosol formulation in the tank 823 unless the valve 5 is opened. Once the valve 5 is opened, the pre-aerosol formulation may exit the tank 823 via the outlet 825 and pass through a nozzle 6. The pre-aerosol formulation may be released for as long as the valve 5 is opened. Since the pre-aerosol formulation is under pressure, the pre-aerosol formulation may exit through the nozzle 6 with sufficient force to shear the pre-aerosol formulation and generate the aerosol.

In some example embodiments, an internal diameter of the nozzle 6 may be chosen to tailor the particle size of the particles in the aerosol. The nozzle 6 may also assist in mechanically shearing the pre-aerosol formulation to generate an aerosol as the pre-aerosol formulation strikes sidewalls of the nozzle 6 and/or is forced therethrough. No heat is applied during formation of the aerosol by the atomizer assembly 721.

In some example embodiments, as shown in FIG. 8, the e-vaping device 60 may include an outlet end insert 20 having at least two off-axis, diverging outlet ports 21. The outlet end insert 20 may be in fluid communication with the mixing chamber 40. As shown in the example embodiment illustrated in FIG. 1B, outlet ports 21 of the outlet end insert 20 may be located at ends of off-axis air passages and may be angled outwardly in relation to the longitudinal direction of the e-vaping device 60 (i.e., divergently). As used herein, the term "off-axis" denotes at an angle to the longitudinal direction of the e-vaping device 60. Thus, the vapor and aerosol may mix to generate a gaseous dispersion that may be drawn through one or more of the outlet ports 21. The gaseous dispersions may be drawn through one or more of the outlets and moves in different directions as compared to e-vaping devices having a single on-axis orifice.

In some example embodiments, the base 71 of the e-vaping device 60 may include a power supply 12, control circuitry 11, and a sensor 13, which may be a sensor. The power supply 12 may include a battery, such as a rechargeable battery.

In some example embodiments, the power supply 12 includes a battery. The battery may be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, the e-vaping device 60 is vapable until the energy in the power supply is depleted. Alternatively, the power supply 12 may be rechargeable and include circuitry allowing the battery to be chargeable by an external charging device. In some example embodiments, the circuitry, when charged, provides power for a desired (or, alternatively a predetermined) number of vapings, after which the circuitry must be re-connected to an external charging device.

In some example embodiments, the heatable portion 119 of the capillary tube 734 may be connected to the power supply 12 by the electrical leads 126*a*, 126*b*. The power supply 12 may be configured to apply voltage across the heatable portion 119 associated with the capillary tube 734 according to a power cycle of either a desired (or, alternatively a predetermined) time period, such as a 2 to 10 second period, or for so long as pressure is applied to the button 600 (shown in FIGS. 6, 11A and 11B).

In some example embodiments, the electrical contacts or connection between the heatable portion 119 and the electrical leads 126*a*, 126*b* are highly conductive and temperature resistant while the heatable portion 119 of the capillary tube 734 is highly resistive so that heat generation occurs primarily along the heatable portion 119 and not at the contacts.

In some example embodiments, the vaporizer assembly 733 produces vapor having particles ranging in size from about 0.4 micron to about 2 microns depending on the pre-vapor formulation included in the tank 732 and the viscosity thereof. The atomizer assembly 721 produces an aerosol having larger particles than the vapor. The particles produced by the atomizer assembly 721 range in size from about 2 microns to about 1 mm.

In some example embodiments, the e-vaping device 60 also includes a control circuitry 11, which may be on a printed circuit board. The control circuitry 11 may be programmable and may include a microprocessor programmed to carry out functions such as heating the capillary tube 734 and/or operating the valves 5, 140. In some example embodiments, the control circuitry 11 may include an application specific integrated circuit (ASIC). In some example embodiments, the power supply 12 may be activated by air being drawn through the outlet end of the e-vaping device 60. The drawing of air is sensed by the sensor 13. The control circuitry 11 sends a signal to the power supply 12 to activate and to open the valves 5, 140 to release a portion of the pre-vapor formulation and a portion of the pre-aerosol formulation.

In some example embodiments, the valves 5, 140 may be electrically operated or mechanically operated. Each valve 5, 140 is configured to maintain the pre-vapor formulation and/or pre-aerosol formulation within the tanks 823, 732, but open when the e-vaping device 60 is activated.

In some example embodiments, the e-vaping device 60 may also include an activation light 48 configured to glow when the vaporizer assembly 733 and the atomizer assembly 721 have been activated. The activation light 48 may include at least one LED and is at a tip end of the e-vaping device 60 so that the activation light 48 takes on the appearance of a burning coal during vaping. Moreover, the activation light 48 may be arranged to be visible to an adult vaper. The activation light 48 may be configured such that the adult vaper may activate and/or deactivate the light 48 when desired.

In some example embodiments, the cartridge 22 and the base 71 include an outer housing 301, 17 extending in a longitudinal direction along the length of the e-vaping device 60.

In some example embodiments, the outer housing 301, 17 of the e-vaping device 60 may be formed of any suitable material or combination of materials. In some example embodiments, the outer housing 301, 17 is formed of metal. Examples of suitable materials include metals, alloys, plastics or composite materials containing one or more of those materials, or thermoplastics that are suitable for food or pharmaceutical applications, for example polypropylene, polyetheretherketone (PEEK), ceramic, low density polyethylene (LDPE) and high density polyethylene (HDPE). In some example embodiments, the material is light and non-brittle. The outer housing 301, 17 may be any suitable color and/or may include graphics or other indicia printed thereon. The outer housing 301, 17 may have a cross-section that is generally round, generally square, generally, triangular, or generally polygonal in shape.

In some example embodiments, the pre-vapor formulation and the pre-aerosol formulation may include common or different ingredients. The pre-vapor formulation and/or the pre-aerosol formulation may include common or different active ingredients and/or flavors. The pre-vapor formulation and/or the pre-aerosol formulation may have common or different viscosities, densities, and/or pH.

In some example embodiments, the pre-vapor formulation and/or the pre-aerosol formulation may be a liquid, solid and/or gel formulation including, but not limited to, water, beads, solvents, active ingredients, ethanol, plant extracts, natural or artificial flavors, and/or vapor formers, such as glycerin and propylene glycol.

In some example embodiments, the tanks 823, 732 each contain different formulations, and each formulation has a different viscosity. In some example embodiments, the pre-vapor formulation may include at least one flavor material, and the pre-aerosol formulation may include at least one tobacco-derived ingredient, such as nicotine.

In some example embodiments, during delivery, the power supply 12 is activated and the heatable portion 119 is heated and a portion of the pre-vapor formulation is vaporized to generate the vapor. Simultaneously, as the pre-aerosol formulation is released through the valve and through the nozzle 6, mechanical forces act upon the pre-aerosol formulation to generate the aerosol. The vapor and the aerosol mix with air that enters the e-vaping device 60 via air inlet ports 44 and generate a gaseous dispersion in a mixing chamber 40.

In some example embodiments, the e-vaping device 60 includes at least one air inlet port 44 configured to deliver air to the mixing chamber 40. The air inlet port 44 and the mixing chamber 40 are arranged between outlets of the vaporizer assembly 733 and the atomizer assembly 721 and the outlet end insert 20. Locating the air inlet port 44 downstream may minimize drawing air along the capillary tube 734, which may cool the capillary tube 734 during heating. In some example embodiments, the at least one air inlet port 44 includes one or two air inlets. In some example embodiments, there may be three, four, five or more air inlet ports 44. Altering the size and number of air inlet ports 44 may also aid in establishing the resistance to draw of the e-vaping device 60.

Figure 9:
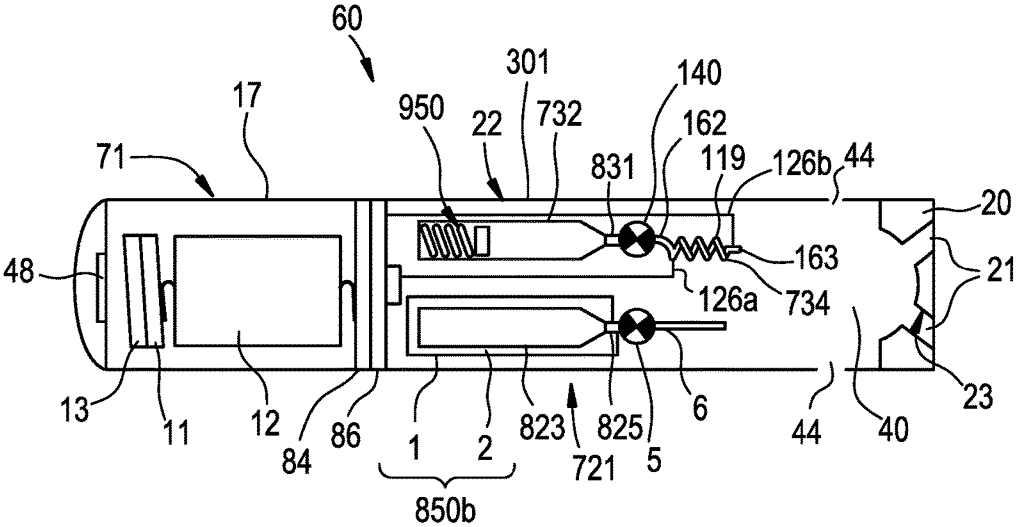
FIG. 9 is a cross-sectional view of the e-vaping device of FIG. 6 according to some example embodiments.

FIG. 9 is a cross-sectional view of the e-vaping device of FIG. 6 according to some example embodiments. The cartridge 22 shown in FIG. 9 may be included in any and all embodiments of cartridges included herein.

In some example embodiments, as shown in FIG. 9, the pressurization arrangement **850*b* of the atomizer assembly 721 may include a container 1 housing a constant pressure fluid 2, such as liquid butane. The tank 823, formed of an elastic material and including flexible walls, is also contained in the container 1**. Because the butane liquid has a higher pressure at room temperature than the pre-aerosol formulation, the pre-aerosol formulation is pressurized. Other suitable high-pressure liquids may be used instead of butane liquid, such as a refrigerant. The refrigerant may be 1,1,1,2-tetrafluoroethane.

Figure 10:
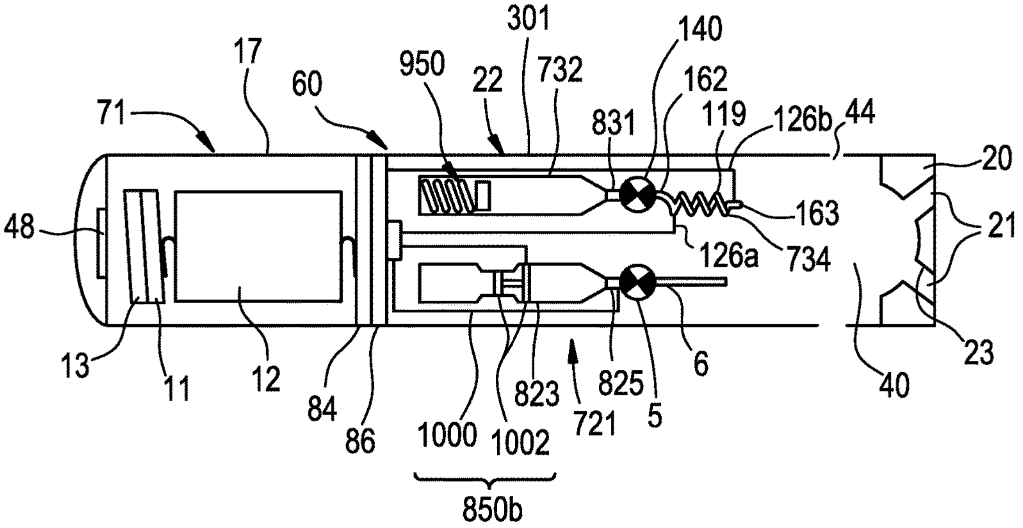
FIG. 10 is a cross-sectional view of the e-vaping device of FIG. 6 according to some example embodiments.

FIG. 10 is a cross-sectional view of the e-vaping device of FIG. 6 according to some example embodiments. The cartridge 22 shown in FIG. 10 may be included in any and all embodiments of cartridges included herein.

In some example embodiments, as shown in FIG. 10, the pressurization arrangement **850*b* of the atomizer assembly 721 may include a carbon dioxide capsule 1000 and a dual piston arrangement 1002 including two pistons with a spring therebetween. The carbon dioxide capsule 1000 may be configured to maintain pressure on the pre-aerosol formulation in the tank 823. The dual piston arrangement 1002 may be configured to at least partially reduce the applied pressure, which may help to maintain the pre-aerosol formulation in the tank 823 until the valve 5** is opened.

Figure 11A:
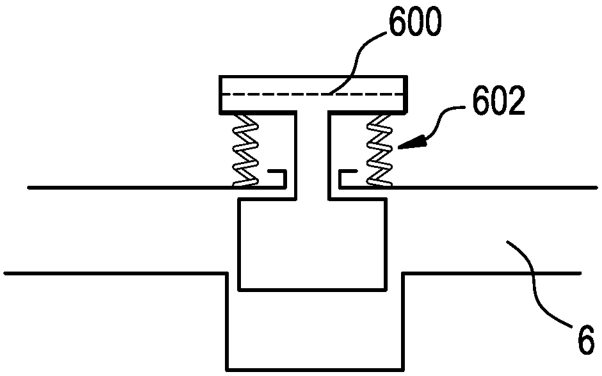
FIG. 11A is an illustration of a push-button valve in a closed position according to some example embodiments.
Figure 11B:
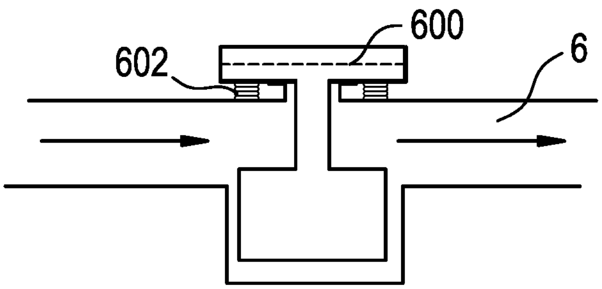
FIG. 11B is an illustration of a push-button valve in an open position according to some example embodiments.

FIG. 11A is an illustration of a push-button valve in a closed position according to some example embodiments. FIG. 11B is an illustration of a push-button valve in an open position according to some example embodiments. The push-button valves shown in FIG. 11A and FIG. 11B may be included in any and all embodiments of e-vaping devices included herein, including one or more of the e-vaping devices 60 shown in any of the figures included and described herein.

In some example embodiments, as shown in FIG. 11A and FIG. 11B, the valves 5, 140 may be mechanically operated. Before and/or during vaping, the adult vaper may press the button 600 (pressure switch). Once the button 600 is pressed, the power supply 12 is activated, the valves 5, 140 are opened, and power is supplied to the heatable portion 119.

In some example embodiments, when the button 600 is used to manually activate the e-vaping device 60, the valves 5, 140 may open when a critical, minimum pressure is reached so as to avoid and/or reduce inadvertent dispensing of formulation material from the tanks 823, 732. In some example embodiments, the pressure required to press the button 600 is high enough such that accidental heating is avoided.

As shown in FIG. 11A and FIG. 11B, in some example embodiments a push-button valve includes one or more springs 602 configured to exert a spring force that resists the button 600 being pressed. In some example embodiments, the force required to press the button 600 to overcome the spring force exerted by the one or more springs 602 is high enough such that accidental heating is avoided.

Figure 12:
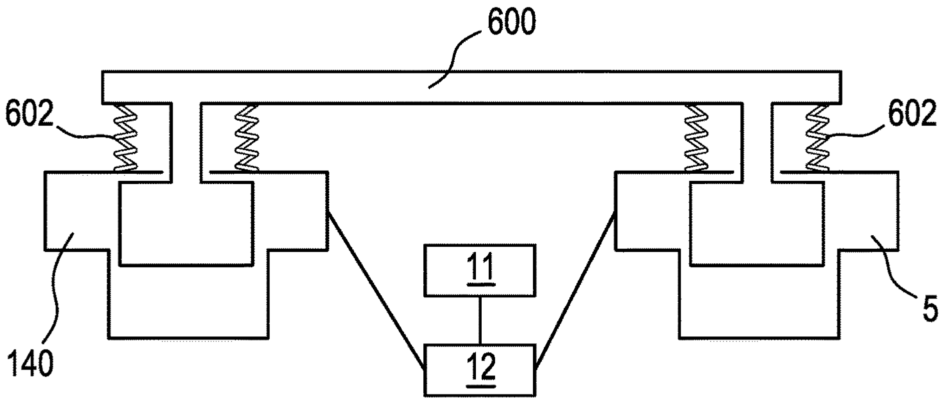
FIG. 12 is an illustration of a push-button valve for use in an e-vaping device according to some example embodiments.

FIG. 12 is an illustration of a push-button valve for use in an e-vaping device according to some example embodiments. The push-button valve shown in FIG. 12 may be included in any and all embodiments of e-vaping devices included herein, including one or more of the e-vaping devices 60 shown in any of the figures included and described herein.

In some example embodiments, as shown in FIG. 12, a single button 600 may be used to open the valves 5, 140 simultaneously. As shown in FIG. 12, the push-button valve may include the button 600 and separate sets of one or more springs 602 may between separate valves 5, 140 and the button 600.

Figure 13:
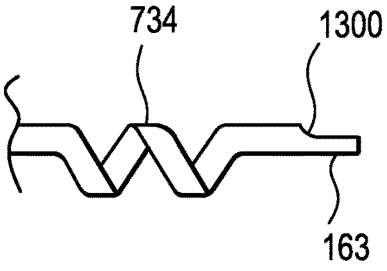
FIG. 13 is an illustration of a heated capillary tube having a constriction therein according to some example embodiments.

FIG. 13 is an illustration of a heated capillary tube having a constriction therein according to some example embodiments. The heated capillary tube shown in FIG. 13 may be included in any and all embodiments of e-vaping devices included herein, including one or more of the e-vaping devices 60 shown in any of the figures included and described herein.

In some example embodiments, as shown in FIG. 13, the capillary tube 734 may include a constriction 1300 adjacent the outlet 163 of the capillary tube 734. While not wishing to be bound by theory, it is believed that the addition of a constriction at the outlet of the capillary tube, which reduces the cross-sectional area of the outlet end, may create sufficiently high shear forces to break up coarse droplets, which may increase the conversion of the pre-vapor formulation to small particles.

In some example embodiments, the e-vaping device 60 may be about 80 mm to about 110 mm long or about 80 mm to about 100 mm long, and about 7 mm to about 8 mm in diameter. In some example embodiments, the e-vaping device 60 is about 84 mm long and has a diameter of about 7.8 mm.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions.

It will now be apparent that a new, improved, and nonobvious e-vaping device has been described in this specification with sufficient particularity as to be understood by one of ordinary skill in the art. While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A base, comprising:

a power supply configured to supply electrical power;

first and second connectors configured to electrically couple separate, respective first and second cartridges to the power supply; and control circuitry configured to independently control dispersion generation by the first and second cartridges, based on cartridge information accessed through the first connector, the second connector, or the first and second connectors, wherein the first cartridge includes a vaporizer assembly and the second cartridge includes an atomizer assembly, the atomizer assembly being configured to generate an aerosol via applying mechanical force to a pre-aerosol formulation, the vaporizer assembly being configured to generate a vapor via heating a pre-vapor formulation.

2. The base of claim 1, wherein the control circuitry is configured to establish a first communication link with a first storage device in the first cartridge via the first connector; and access the cartridge information from the first storage device via the first communication link, the cartridge information being associated with the first cartridge.

3. The base of claim 1, wherein the cartridge information includes, information uniquely identifying one or more elements of a dispersion generator included in the first cartridge, information indicating a dispersion generator "type" of a dispersion generator included in the first cartridge, information associated with a formulation held in the first cartridge, a particular activation sequence associated with a dispersion generator included in the first cartridge, a sub-combination thereof, or a combination thereof.

4. The base of claim 1, wherein the control circuitry is configured to independently control dispersion generation by the first and second cartridges based on independent control of electrical power supplied from the power supply to the first cartridge via the first connector and to the second cartridge via the second connector.

5. The base of claim 4, wherein the control circuitry is configured to independently control the electrical power supplied to the first and second connectors, such that electrical power is supplied to the first and second cartridges at different times.

6. The base of claim 4, wherein the control circuitry is configured to independently control the electrical power supplied to the first and second connectors, such that electrical power is supplied to the first and second cartridges in an alternating pattern in response to successive vaping command signals.

7. The base of claim 1, wherein the power supply includes a rechargeable battery.

8. A base, comprising:

a power supply configured to supply electrical power;

first and second connectors configured to electrically couple separate, respective first and second cartridges to the power supply; and control circuitry configured to independently control dispersion generation by the first and second cartridges, based on cartridge information accessed through the first connector, the second connector, or the first and second connectors, wherein the control circuitry is configured to independently control dispersion generation by the first and second cartridges based on independent control of electrical power supplied from the power supply to the first cartridge via the first connector and to the second cartridge via the second connector, wherein the control circuitry is configured to independently control the electrical power supplied to the first and second connectors, such that a dispersion generator included in the second cartridge generates a dispersion based on heat generated by a dispersion generator included in the first cartridge.

9. An e-vaping device, comprising:

a power supply configured to supply electrical power;

first and second cartridges electrically coupled to the power supply; and control circuitry configured to independently control dispersion generation by the first and second cartridges, based on accessing cartridge information from the first cartridge, the second cartridge, or the first and second cartridges, wherein the first cartridge includes a vaporizer assembly and the second cartridge includes an atomizer assembly, the atomizer assembly being configured to generate an aerosol via applying mechanical force to a pre-aerosol formulation, the vaporizer assembly being configured to generate a vapor via heating a pre-vapor formulation.

10. The e-vaping device of claim 9, wherein the control circuitry is configured to establish a first communication link with a first storage device in the first cartridge; and access the cartridge information from the first storage device via the first communication link, the cartridge information being associated with the first cartridge.

11. The e-vaping device of claim 9, wherein the cartridge information includes, information uniquely identifying one or more elements of a dispersion generator included in the first cartridge, information indicating a dispersion generator "type" of a dispersion generator included in the first cartridge, information associated with a formulation held in the first cartridge, a particular activation sequence associated with a dispersion generator included in the first cartridge, a sub-combination thereof, or a combination thereof.

12. The e-vaping device of claim 9, wherein the control circuitry is configured to independently control dispersion generation by the first and second cartridges based on independent control of electrical power supplied from the power supply to the first cartridge via a first connector and to the second cartridges via a second connectors.

13. The e-vaping device of claim 12, wherein the control circuitry is configured to independently control the electrical power supplied to the first and second cartridges, such that electrical power is supplied to the first and second cartridges at different times.

14. The e-vaping device of claim 12, wherein the control circuitry is configured to independently control the electrical power supplied to the first and second cartridges, such that electrical power is supplied to the first and second cartridges in an alternating pattern in response to successive vaping command signals.

15. The e-vaping device of claim 9, wherein the power supply includes a rechargeable battery.

16. An e-vaping device, comprising:

a power supply configured to supply electrical power;

first and second cartridges electrically coupled to the power supply; and control circuitry configured to independently control dispersion generation by the first and second cartridges, based on accessing cartridge information from the first cartridge, the second cartridge, or the first and second cartridges, wherein the control circuitry is configured to independently control dispersion generation by the first and second cartridges based on independent control of electrical power supplied from the power supply to the first cartridge via a first connector and to the second cartridge via a second connector, wherein the control circuitry is configured to independently control the electrical power supplied to the first and second cartridges, such that a dispersion generator included in the second cartridge generates a dispersion based on heat generated by a dispersion generator included in the first cartridge.

17. A method comprising:

independently controlling dispersion generation by first and second cartridges electrically coupled to a power supply of a base, the independently controlling including, establishing a first communication link with a first storage device in the first cartridge via a first connector;

accessing cartridge information associated with the first cartridge from the first storage device via the first communication link; and independently controlling electrical power supplied to the first cartridge, based on the accessed cartridge information, such that a dispersion generator included in the second cartridge generates a dispersion based on heat generated by a dispersion generator included in the first cartridge.

18. A base, comprising:

a power supply configured to supply electrical power;

first and second connectors configured to electrically couple separate, respective first and second cartridges to the power supply;

a cover configured to establish a removable enclosure of the first and second connectors; and control circuitry configured to independently control dispersion generation by the first and second cartridges, based on cartridge information accessed through the first connector, the second connector, or the first and second connectors, wherein the first cartridge includes a vaporizer assembly and the second cartridge includes an atomizer assembly, the atomizer assembly being configured to generate an aerosol via applying mechanical force to a pre-aerosol formulation, the vaporizer assembly being configured to generate a vapor via heating a pre-vapor formulation.

19. A base, comprising:

a power supply configured to supply electrical power;

first and second connectors configured to electrically couple separate, respective first and second cartridges to the power supply;

a cover configured to establish a removable enclosure of the first and second connectors; and control circuitry configured to independently control dispersion generation by the first and second cartridges, based on cartridge information accessed through the first connector, the second connector, or the first and second connectors, wherein the control circuitry is configured to independently control dispersion generation by the first and second cartridges based on independent control of electrical power supplied from the power supply to the first cartridge via the first connector and to the second cartridge via the second connector, wherein the control circuitry is configured to independently control the electrical power supplied to the first and second connectors, such that a dispersion generator included in the second cartridge generates a dispersion based on heat generated by a dispersion generator included in the first cartridge.

20. A method, comprising:

independently controlling dispersion generation by first and second cartridges electrically coupled to a power supply of a base, the independently controlling including, establishing a first communication link with a first storage device in the first cartridge via a first connector;

accessing cartridge information associated with the first cartridge from the first storage device via the first communication link; and independently controlling electrical power supplied to the first cartridge based on the accessed cartridge information, wherein the first cartridge includes a vaporizer assembly and the second cartridge includes an atomizer assembly, the atomizer assembly being configured to generate an aerosol via applying mechanical force to a pre-aerosol formulation, the vaporizer assembly being configured to generate a vapor via heating a pre-vapor formulation.

21. The method of claim 20, further comprising:

independently controlling electrical power supplied to the first and second cartridges, such that electrical power is supplied to the first and second cartridges at different times.

22. The method of claim 20, further comprising:

independently controlling electrical power supplied to the first and second cartridges, such that electrical power is supplied to the first and second cartridges in an alternating pattern in response to successive vaping command signals.

* * * * *